United States Patent
Purdy et al.

(10) Patent No.: US 10,478,241 B2
(45) Date of Patent: Nov. 19, 2019

(54) ARTICULATING OSTEOTOME WITH CEMENT DELIVERY CHANNEL

(71) Applicant: DFINE, INC., South Jordan, UT (US)

(72) Inventors: Craig Purdy, Sunnyvale, CA (US); Dan Balbierz, Redwood City, CA (US)

(73) Assignee: Merit Medical Systems, Inc., South Jordan, UT (US)

( * ) Notice: Subject to any disclaimer, the term of this patent is extended or adjusted under 35 U.S.C. 154(b) by 162 days.

(21) Appl. No.: 15/793,509

(22) Filed: Oct. 25, 2017

(65) Prior Publication Data

US 2018/0116702 A1 May 3, 2018

Related U.S. Application Data

(60) Provisional application No. 62/413,768, filed on Oct. 27, 2016.

(51) Int. Cl.
| | |
|---|---|
| *A61B 17/58* | (2006.01) |
| *A61B 17/60* | (2006.01) |
| *A61F 2/00* | (2006.01) |
| *A61B 17/88* | (2006.01) |
| *A61B 17/16* | (2006.01) |
| *A61B 18/00* | (2006.01) |

(52) U.S. Cl.
CPC ...... *A61B 17/8811* (2013.01); *A61B 17/1671* (2013.01); *A61B 17/8819* (2013.01); *A61B 17/1642* (2013.01); *A61B 2018/00339* (2013.01)

(58) Field of Classification Search
CPC combination set(s) only.
See application file for complete search history.

(56) References Cited

U.S. PATENT DOCUMENTS

| | | |
|---|---|---|
| 2,688,329 A | 9/1954 | Wallace |
| 3,140,623 A | 7/1964 | Hoose |
| 3,228,400 A | 1/1966 | Armao |
| 3,503,385 A | 3/1970 | Stevens |
| 3,625,200 A | 12/1971 | Muller |
| 3,664,344 A | 5/1972 | Bryne |
| 3,794,039 A | 2/1974 | Kollner et al. |
| 3,908,637 A | 9/1975 | Doroshow |

(Continued)

FOREIGN PATENT DOCUMENTS

| | | |
|---|---|---|
| CA | 2785207 | 7/2011 |
| CN | 88203061 | 11/1988 |

(Continued)

OTHER PUBLICATIONS

US 7,063,700 B2, 06/2006, Michelson (withdrawn)

(Continued)

*Primary Examiner* — Sameh R Boles
(74) *Attorney, Agent, or Firm* — Stoel Rives LLP

(57) ABSTRACT

The present disclosure illustrates an osteotome for treating hard tissue. The osteotome embodiments described herein include a shaft with a working end configured to displace hard tissue and a lumen to deliver material through the shaft. The working end may create pathways by selectively transitioning from a linear to a non-linear configuration. The lumen may deliver material through the shaft while the working end is in a linear or a non-linear configuration allowing precise filling of the pathways.

20 Claims, 10 Drawing Sheets

(56) References Cited

U.S. PATENT DOCUMENTS

| | | |
|---|---|---|
| 4,033,331 A | 7/1977 | Guss et al. |
| 4,131,597 A | 12/1978 | Bluethgen et al. |
| 4,236,520 A | 12/1980 | Anderson |
| 4,276,860 A | 7/1981 | Malmin |
| 4,294,251 A | 10/1981 | Grennwald et al. |
| 4,337,773 A | 7/1982 | Raftopoulos et al. |
| 4,386,717 A | 6/1983 | Koob |
| 4,399,814 A | 8/1983 | Pratt, Jr. et al. |
| 4,411,266 A | 10/1983 | Cosman |
| 4,456,017 A | 6/1984 | Miles |
| 4,473,077 A | 9/1984 | Noiles |
| 4,476,861 A | 10/1984 | Dimakos et al. |
| 4,578,061 A | 3/1986 | Lemelson |
| 4,586,923 A | 5/1986 | Gould et al. |
| 4,595,006 A | 6/1986 | Burke et al. |
| 4,619,263 A | 10/1986 | Frisbie et al. |
| 4,627,434 A | 12/1986 | Murray |
| 4,641,654 A | 2/1987 | Samson et al. |
| 4,653,489 A | 3/1987 | Tronzo |
| 4,668,295 A | 5/1987 | Bajpai |
| 4,719,968 A | 1/1988 | Speros |
| 4,722,948 A | 2/1988 | Sanderson |
| 4,731,054 A | 3/1988 | Billeter et al. |
| 4,742,817 A | 5/1988 | Kawashima et al. |
| 4,747,840 A | 5/1988 | Ladika et al. |
| 4,748,969 A | 6/1988 | Wardle |
| 4,784,638 A | 11/1988 | Ghajar et al. |
| 4,795,602 A | 1/1989 | Pretchel et al. |
| 4,842,603 A | 6/1989 | Draenert |
| 4,843,112 A | 6/1989 | Gerhart et al. |
| 4,846,814 A | 7/1989 | Ruiz |
| 4,865,586 A | 9/1989 | Hedberg |
| 4,869,906 A | 9/1989 | Dingeldein et al. |
| 4,888,366 A | 12/1989 | Chu et al. |
| 4,900,303 A | 2/1990 | Lemelson |
| 4,961,730 A | 10/1990 | Bodicky et al. |
| 4,961,731 A | 10/1990 | Bodicky |
| 4,963,151 A | 10/1990 | Ducheyne et al. |
| 4,969,870 A | 11/1990 | Kramer et al. |
| 4,969,888 A | 11/1990 | Scholten et al. |
| 4,982,730 A | 1/1991 | Royce |
| 5,059,193 A | 1/1991 | Kuslich |
| 4,998,923 A | 3/1991 | Samson et al. |
| 5,004,501 A | 4/1991 | Faccioli |
| 5,017,627 A | 5/1991 | Bonfield |
| 5,046,513 A | 9/1991 | O'Leary et al. |
| 5,049,137 A | 9/1991 | Thompson |
| 5,049,157 A | 9/1991 | Mittelmeier et al. |
| 5,085,861 A | 2/1992 | Gerhart et al. |
| 5,088,991 A | 2/1992 | Weldon |
| 5,116,305 A | 2/1992 | Milder et al. |
| 5,092,891 A | 3/1992 | Kummer et al. |
| 5,103,804 A | 4/1992 | Abele |
| 5,108,404 A | 4/1992 | Scholten et al. |
| 5,112,303 A | 5/1992 | Pudenz et al. |
| 5,114,414 A | 5/1992 | Buchbinder |
| 5,147,334 A | 9/1992 | Moss |
| 5,156,606 A | 10/1992 | Chin |
| 5,163,431 A | 11/1992 | Greip |
| 5,184,757 A | 2/1993 | Giannuzzi |
| 5,188,619 A | 2/1993 | Myers |
| 5,196,201 A | 3/1993 | Larsson et al. |
| 5,197,971 A | 3/1993 | Bonutti |
| 5,211,631 A | 5/1993 | Sheaff |
| 5,231,989 A | 8/1993 | Middleman et al. |
| 5,242,082 A | 9/1993 | Giannuzzi |
| 5,264,214 A | 11/1993 | Rhee et al. |
| 5,266,248 A | 11/1993 | Ohtsuka et al. |
| 5,269,750 A | 12/1993 | Grulke et al. |
| 5,282,821 A | 2/1994 | Donahue |
| 5,284,128 A | 2/1994 | Hart |
| 5,285,795 A | 2/1994 | Ryan et al. |
| 5,295,980 A | 3/1994 | Ersek |
| 5,296,026 A | 3/1994 | Monroe et al. |
| 5,308,342 A | 5/1994 | Sepetka et al. |
| 5,322,064 A | 6/1994 | Lundquist |
| 5,322,505 A | 6/1994 | Krause et al. |
| 5,334,181 A | 8/1994 | Rubinsky et al. |
| 5,336,699 A | 8/1994 | Cooke et al. |
| 5,343,877 A | 9/1994 | Park |
| 5,352,715 A | 10/1994 | Wallace et al. |
| 5,356,629 A | 10/1994 | Sander |
| 5,360,416 A | 11/1994 | Ausherman et al. |
| 5,368,598 A | 11/1994 | Hasson |
| 5,372,587 A | 12/1994 | Hammerslag et al. |
| 5,378,234 A | 1/1995 | Hammerslag et al. |
| 5,380,307 A | 1/1995 | Chee et al. |
| 5,385,563 A | 1/1995 | Groos |
| 5,389,073 A | 2/1995 | Imran |
| 5,425,770 A | 6/1995 | Piez et al. |
| 5,431,168 A | 7/1995 | Webster, Jr. |
| 5,431,639 A | 7/1995 | Shaw |
| 5,437,636 A | 8/1995 | Snoke et al. |
| 5,449,301 A | 9/1995 | Hanna et al. |
| 5,449,351 A | 9/1995 | Zohmann |
| 5,458,597 A | 10/1995 | Edwards et al. |
| 5,480,382 A | 1/1996 | Hammerslag et al. |
| 5,484,424 A | 1/1996 | Cottenceau et al. |
| 5,489,275 A | 2/1996 | Thompson et al. |
| 5,496,330 A | 3/1996 | Bates et al. |
| 5,512,610 A | 4/1996 | Lin |
| 5,514,130 A | 5/1996 | Baker |
| 5,514,137 A | 5/1996 | Coutts |
| 5,531,715 A | 7/1996 | Engelson et al. |
| 5,535,922 A | 7/1996 | Maziarz |
| 5,549,542 A | 8/1996 | Kovalcheck |
| 5,549,679 A | 8/1996 | Kuslich |
| 5,554,114 A | 9/1996 | Wallace et al. |
| 5,571,085 A | 11/1996 | Accisano, III |
| 5,571,088 A | 11/1996 | Lennox |
| 5,574,075 A | 11/1996 | Draemert |
| 5,599,346 A | 2/1997 | Edwards et al. |
| 5,616,121 A | 4/1997 | McKay |
| 5,620,447 A | 4/1997 | Smith et al. |
| 5,620,467 A | 4/1997 | Wagner |
| 5,624,396 A | 4/1997 | McNamara et al. |
| 5,628,771 A | 5/1997 | Mizukawa et al. |
| 5,637,090 A | 6/1997 | McGee |
| 5,637,091 A | 6/1997 | Hakky et al. |
| 5,662,680 A | 9/1997 | Desai |
| 5,681,282 A | 10/1997 | Eggers et al. |
| 5,681,289 A | 10/1997 | Wilcox et al. |
| 5,681,317 A | 10/1997 | Caldarise |
| 5,685,826 A | 11/1997 | Bonutti |
| 5,695,513 A | 12/1997 | Johnson et al. |
| 5,697,536 A | 12/1997 | Eggers et al. |
| 5,697,909 A | 12/1997 | Eggers et al. |
| 5,700,157 A | 12/1997 | Chung |
| 5,704,926 A | 1/1998 | Sutton |
| 5,709,697 A | 1/1998 | Ratcliff et al. |
| 5,725,568 A | 3/1998 | Hastings |
| 5,735,829 A | 4/1998 | Cherian |
| 5,741,320 A | 4/1998 | Thornton et al. |
| 5,766,153 A | 6/1998 | Eggers et al. |
| 5,800,408 A | 9/1998 | Strauss et al. |
| 5,810,804 A | 9/1998 | Gough |
| 5,810,867 A | 9/1998 | Zarbateny et al. |
| 5,820,592 A | 10/1998 | Hammerslag et al. |
| 5,833,632 A | 11/1998 | Jacobsen et al. |
| 5,833,692 A | 11/1998 | Cesarini et al. |
| 5,847,046 A | 12/1998 | Jiang et al. |
| 5,849,028 A | 12/1998 | Chen |
| 5,851,212 A | 12/1998 | Zirps et al. |
| 5,855,577 A | 1/1999 | Murphy-Chutorian et al. |
| 5,858,003 A | 1/1999 | Atala |
| 5,860,952 A | 1/1999 | Quinn |
| 5,860,974 A | 1/1999 | Abele |
| 5,876,373 A | 3/1999 | Giba et al. |
| 5,891,027 A | 4/1999 | Tu |
| 5,902,251 A | 5/1999 | VanHooydonk |
| 5,902,839 A | 5/1999 | Lautenschlager et al. |
| 5,914,356 A | 6/1999 | Erbe |
| 5,921,956 A | 7/1999 | Grinberg et al. |
| 5,928,239 A | 7/1999 | Mirza |

(56) References Cited

U.S. PATENT DOCUMENTS

| | | |
|---|---|---|
| 5,931,829 A | 8/1999 | Burbank et al. |
| 5,944,715 A | 8/1999 | Goble et al. |
| 5,947,964 A | 9/1999 | Eggers |
| 5,972,015 A | 10/1999 | Scribner et al. |
| 5,997,561 A | 12/1999 | Khalili |
| 6,019,765 A | 2/2000 | Thornhill et al. |
| 6,027,487 A | 2/2000 | Crocker |
| 6,030,360 A | 2/2000 | Biggs |
| 6,048,346 A | 4/2000 | Reiley et al. |
| 6,059,739 A | 5/2000 | Baumann |
| 6,063,078 A | 5/2000 | Wittkampf |
| 6,064,902 A | 5/2000 | Haissaguerre |
| 6,066,154 A | 5/2000 | Reiley et al. |
| 6,066,176 A | 5/2000 | Oshida |
| 6,073,051 A | 6/2000 | Sharkey et al. |
| 6,080,801 A | 6/2000 | Draenert et al. |
| 6,099,514 A | 8/2000 | Sharkey et al. |
| 6,106,524 A | 8/2000 | Eggers et al. |
| 6,106,539 A | 8/2000 | Fortier |
| 6,110,155 A | 8/2000 | Baudino |
| 6,123,702 A | 9/2000 | Swanson |
| 6,127,597 A | 10/2000 | Beyar et al. |
| 6,135,999 A | 10/2000 | Fanton et al. |
| 6,146,355 A | 11/2000 | Biggs |
| 6,156,254 A | 12/2000 | Andrews et al. |
| 6,183,435 B1 | 2/2001 | Bumbalough et al. |
| 6,203,507 B1 | 3/2001 | Wadsworth et al. |
| 6,203,574 B1 | 3/2001 | Kawamura |
| 6,228,052 B1 | 5/2001 | Pohndorf |
| 6,228,904 B1 | 5/2001 | Yadav et al. |
| 6,231,569 B1 | 5/2001 | Bek et al. |
| 6,231,615 B1 | 5/2001 | Preissman |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,251,092 B1 | 6/2001 | Qin et al. |
| 6,258,086 B1 | 7/2001 | Ashley et al. |
| 6,270,476 B1 | 8/2001 | Santoianni et al. |
| 6,280,413 B1 | 8/2001 | Clark et al. |
| 6,280,434 B1 | 8/2001 | Kinoshita et al. |
| 6,280,441 B1 | 8/2001 | Ryan |
| 6,280,456 B1 | 8/2001 | Scribner et al. |
| 6,280,473 B1 | 8/2001 | Lemperle et al. |
| 6,283,960 B1 | 9/2001 | Ashley |
| 6,291,547 B1 | 9/2001 | Lyles |
| 6,312,428 B1 | 11/2001 | Eggers |
| 6,312,454 B1 | 11/2001 | Stockel et al. |
| 6,332,894 B1 | 12/2001 | Stalcup et al. |
| 6,348,055 B1 | 2/2002 | Preissman |
| 6,352,533 B1 | 3/2002 | Ellman et al. |
| 6,358,251 B1 | 3/2002 | Mirza |
| 6,375,659 B1 | 4/2002 | Erbe et al. |
| 6,383,188 B2 | 5/2002 | Kuslich et al. |
| 6,383,190 B1 | 5/2002 | Preissman |
| 6,395,007 B1 | 5/2002 | Bhatnagar et al. |
| 6,408,889 B1 | 6/2002 | Komachi |
| 6,409,722 B1 | 6/2002 | Hoey et al. |
| 6,428,894 B1 | 8/2002 | Babich et al. |
| 6,437,019 B1 | 8/2002 | Rusin et al. |
| 6,440,138 B1 | 8/2002 | Reiley et al. |
| 6,447,506 B1 | 9/2002 | Swanson et al. |
| 6,447,514 B1 | 9/2002 | Stalcup et al. |
| 6,464,683 B1 | 10/2002 | Samuelson et al. |
| 6,478,793 B1 | 11/2002 | Cosman et al. |
| 6,479,565 B1 | 11/2002 | Stanley |
| 6,484,904 B1 | 11/2002 | Horner et al. |
| 6,506,217 B1 | 1/2003 | Arnett |
| 6,511,471 B2 | 1/2003 | Rosenman et al. |
| 6,524,296 B1 | 2/2003 | Beals |
| 6,565,588 B1 | 5/2003 | Clement et al. |
| 6,575,969 B1 | 6/2003 | Rittman et al. |
| 6,575,978 B2 | 6/2003 | Peterson et al. |
| 6,576,249 B1 | 6/2003 | Gendler et al. |
| 6,582,446 B1 | 6/2003 | Marchosky |
| 6,592,559 B1 | 7/2003 | Pakter et al. |
| 6,599,961 B1 | 7/2003 | Pienkowski et al. |
| 6,620,162 B2 | 7/2003 | Kuslich et al. |
| 6,602,248 B1 | 8/2003 | Sharps et al. |
| 6,607,544 B1 | 8/2003 | Boucher et al. |
| 6,613,054 B2 | 9/2003 | Scribner et al. |
| 6,622,731 B2 | 9/2003 | Daniel et al. |
| 6,623,448 B2 | 9/2003 | Slater |
| 6,638,268 B2 | 10/2003 | Niazi |
| 6,663,647 B2 | 10/2003 | Reiley et al. |
| 6,641,587 B2 | 11/2003 | Scribner et al. |
| 6,645,213 B2 | 11/2003 | Sand et al. |
| 6,676,665 B2 | 1/2004 | Foley et al. |
| 6,679,886 B2 | 1/2004 | Weikel et al. |
| 6,689,823 B1 | 2/2004 | Bellare et al. |
| 6,692,532 B1 | 2/2004 | Healy et al. |
| 6,716,216 B1 | 4/2004 | Boucher et al. |
| 6,719,761 B1 | 4/2004 | Reiley et al. |
| 6,719,773 B1 | 4/2004 | Boucher et al. |
| 6,726,691 B2 | 4/2004 | Osorio et al. |
| 6,730,095 B2 | 5/2004 | Olson, Jr. et al. |
| 6,740,090 B2 | 5/2004 | Cragg et al. |
| 6,740,093 B2 | 5/2004 | Hochschuler et al. |
| 6,743,239 B1 | 6/2004 | Kuehn et al. |
| 6,746,451 B2 | 6/2004 | Middleton et al. |
| 6,752,863 B2 | 6/2004 | Lyles et al. |
| 6,753,007 B2 | 6/2004 | Haggard et al. |
| 6,770,079 B2 | 8/2004 | Bhatnagar et al. |
| 6,814,734 B2 | 11/2004 | Chappuis et al. |
| 6,814,736 B2 | 11/2004 | Reiley et al. |
| 6,818,001 B2 | 11/2004 | Wulfman et al. |
| 6,832,984 B2 | 12/2004 | Stelzer et al. |
| 6,835,193 B2 | 12/2004 | Epstein et al. |
| 6,837,867 B2 | 1/2005 | Kortelling |
| 6,863,672 B2 | 3/2005 | Reiley et al. |
| 6,869,430 B2 | 3/2005 | Balbierz et al. |
| 6,869,445 B1 | 3/2005 | Johnson |
| 6,875,219 B2 | 4/2005 | Arramon |
| 6,881,214 B2 | 4/2005 | Cosman et al. |
| 6,887,246 B2 | 5/2005 | Bhatnagar et al. |
| 6,899,715 B1 | 5/2005 | Beaty |
| 6,899,719 B2 | 5/2005 | Reiley et al. |
| 6,907,884 B2 | 6/2005 | Pellegrino et al. |
| 6,913,594 B2 | 7/2005 | Coleman et al. |
| 6,916,306 B1 | 7/2005 | Jenkins et al. |
| 6,923,813 B2 | 8/2005 | Phillips |
| 6,945,956 B2 | 9/2005 | Waldhauser et al. |
| 6,953,594 B2 | 10/2005 | Lee et al. |
| 6,955,716 B2 | 10/2005 | Xu et al. |
| 6,976,987 B2 | 12/2005 | Flores |
| 6,979,312 B2 | 12/2005 | Shimada |
| 6,979,352 B2 | 12/2005 | Reynolds |
| 6,981,981 B2 | 1/2006 | Reiley et al. |
| 6,991,616 B2 | 1/2006 | Bencini et al. |
| 6,998,128 B2 | 2/2006 | Haggard et al. |
| 7,004,930 B2 | 2/2006 | Marshall |
| 7,004,945 B2 | 2/2006 | Boyd et al. |
| 7,008,433 B2 | 3/2006 | Voellmicke et al. |
| 7,018,460 B2 | 3/2006 | Xu et al. |
| 7,022,133 B2 | 4/2006 | Yee et al. |
| 7,029,468 B2 | 4/2006 | Honebrink |
| 7,044,954 B2 | 5/2006 | Reiley et al. |
| 7,059,330 B1 | 6/2006 | Makower et al. |
| 7,063,682 B1 | 6/2006 | Whayne et al. |
| 7,066,942 B2 | 6/2006 | Treace |
| RE39,196 E | 7/2006 | Ying et al. |
| 7,081,122 B1 | 7/2006 | Reiley et al. |
| 7,081,161 B2 | 7/2006 | Genge et al. |
| 7,091,258 B2 | 8/2006 | Neubert et al. |
| 7,091,260 B2 | 8/2006 | Kühn |
| 7,094,202 B2 | 8/2006 | Nobis et al. |
| 7,094,286 B2 | 8/2006 | Liu |
| 7,108,696 B2 | 9/2006 | Daniel et al. |
| 7,109,254 B2 | 9/2006 | Müller et al. |
| 7,112,205 B2 | 9/2006 | Carrison |
| 7,114,501 B2 | 10/2006 | Johnson et al. |
| 7,138,442 B2 | 11/2006 | Smith et al. |
| 7,153,306 B2 | 12/2006 | Ralph et al. |
| 7,153,307 B2 | 12/2006 | Scribner et al. |
| 7,156,843 B2 | 1/2007 | Skarda |

(56) References Cited

U.S. PATENT DOCUMENTS

| | | |
|---|---|---|
| 7,156,845 B2 | 1/2007 | Mulier |
| 7,166,121 B2 | 1/2007 | Reiley et al. |
| 7,172,629 B2 | 2/2007 | McKay et al. |
| 7,179,255 B2 | 2/2007 | Lettice et al. |
| 7,186,234 B2 | 3/2007 | Dahla et al. |
| 7,186,761 B2 | 3/2007 | Soffiati et al. |
| 7,226,481 B2 | 6/2007 | Kuslich et al. |
| 7,252,671 B2 | 8/2007 | Scribner et al. |
| 7,160,296 B2 | 9/2007 | Pearson et al. |
| 7,267,683 B2 | 9/2007 | Sharkey et al. |
| 7,270,661 B2 | 9/2007 | Dahla et al. |
| 7,294,127 B2 | 11/2007 | Leung |
| 7,465,318 B2 | 12/2008 | Sennett et al. |
| 7,480,533 B2 | 1/2009 | Cosman et al. |
| 7,503,920 B2 | 3/2009 | Siegal |
| 7,544,196 B2 | 6/2009 | Bagga et al. |
| 7,559,932 B2 | 7/2009 | Truckai et al. |
| 7,569,054 B2 | 8/2009 | Michelson |
| 7,572,263 B2 | 8/2009 | Preissman |
| 7,591,822 B2 | 9/2009 | Olson, Jr. et al. |
| 7,625,364 B2 | 12/2009 | Corcoran et al. |
| 7,641,664 B2 | 1/2010 | Pagano |
| 7,731,720 B2 | 6/2010 | Sand et al. |
| 7,811,291 B2 | 10/2010 | Liu et al. |
| 7,824,403 B2 | 11/2010 | Vaska |
| 7,842,041 B2 | 11/2010 | Liu et al. |
| 7,887,543 B2 | 2/2011 | Sand et al. |
| 7,905,884 B2 | 3/2011 | Simonton et al. |
| 7,918,874 B2 | 4/2011 | Siegal |
| 7,972,340 B2 | 7/2011 | Sand et al. |
| 7,976,542 B1 | 7/2011 | Cosman |
| 8,034,071 B2 | 10/2011 | Scribner et al. |
| 8,246,627 B2 | 8/2012 | Vanleeuwen et al. |
| 8,284,128 B2 | 10/2012 | Kimura |
| 8,518,036 B2 | 8/2013 | Leung |
| 8,583,260 B2 | 11/2013 | Knudson |
| 8,591,507 B2 | 11/2013 | Kramer et al. |
| 8,663,226 B2 | 3/2014 | Germain |
| RE44,883 E | 5/2014 | Cha |
| 8,758,349 B2 | 6/2014 | Germain et al. |
| 8,827,981 B2 | 9/2014 | Liu et al. |
| 8,864,760 B2 | 10/2014 | Kramer et al. |
| 8,936,631 B2 | 1/2015 | Nguyen |
| 9,113,974 B2 | 8/2015 | Germain |
| 9,125,671 B2 | 9/2015 | Germain et al. |
| 9,161,809 B2 | 10/2015 | Germain et al. |
| 9,421,057 B2 | 8/2016 | Germain |
| 9,743,938 B2 | 8/2017 | Germain et al. |
| 2001/0011174 A1 | 8/2001 | Reiley et al. |
| 2001/0023349 A1 | 9/2001 | Van Tassel et al. |
| 2002/0007180 A1 | 1/2002 | Wittenberger et al. |
| 2002/0013600 A1 | 1/2002 | Scribner et al. |
| 2002/0026195 A1 | 2/2002 | Layne et al. |
| 2002/0026197 A1 | 2/2002 | Foley et al. |
| 2002/0068929 A1 | 6/2002 | Zvuloni |
| 2002/0068974 A1 | 6/2002 | Kuslich et al. |
| 2002/0077595 A1 | 6/2002 | Hundertmark et al. |
| 2002/0082605 A1 | 6/2002 | Reiley et al. |
| 2002/0115742 A1 | 8/2002 | Trieu et al. |
| 2002/0128638 A1 | 9/2002 | Chauvel et al. |
| 2002/0133148 A1 | 9/2002 | Daniel et al. |
| 2002/0156483 A1 | 10/2002 | Voellmicke et al. |
| 2002/0188299 A1 | 12/2002 | Reiley et al. |
| 2002/0188300 A1 | 12/2002 | Arramon et al. |
| 2003/0014094 A1 | 1/2003 | Hammack et al. |
| 2003/0032929 A1 | 2/2003 | McGuckin |
| 2003/0036763 A1 | 2/2003 | Bhatnagar et al. |
| 2003/0043963 A1 | 3/2003 | Yamagami et al. |
| 2003/0050644 A1 | 3/2003 | Boucher et al. |
| 2003/0069522 A1 | 4/2003 | Jacobsen et al. |
| 2003/0073979 A1 | 4/2003 | Naimark et al. |
| 2003/0130664 A1 | 7/2003 | Boucher et al. |
| 2003/0163085 A1 | 8/2003 | Tanner et al. |
| 2003/0171744 A1 | 9/2003 | Leung et al. |
| 2003/0191489 A1 | 10/2003 | Reiley et al. |
| 2003/0195547 A1 | 10/2003 | Scribner et al. |
| 2003/0212394 A1 | 11/2003 | Pearson et al. |
| 2003/0212395 A1 | 11/2003 | Woloszko et al. |
| 2003/0220414 A1 | 11/2003 | Axen et al. |
| 2003/0225432 A1 | 12/2003 | Baptiste et al. |
| 2003/0233096 A1 | 12/2003 | Osorio et al. |
| 2004/0023384 A1 | 2/2004 | Fukaya |
| 2004/0023784 A1 | 2/2004 | Yu et al. |
| 2004/0024081 A1 | 2/2004 | Trieu et al. |
| 2004/0024398 A1 | 2/2004 | Hovda et al. |
| 2004/0024409 A1 | 2/2004 | Sand et al. |
| 2004/0024410 A1 | 2/2004 | Olson et al. |
| 2004/0034384 A1 | 2/2004 | Fukaya |
| 2004/0044096 A1 | 3/2004 | Smith et al. |
| 2004/0044350 A1 | 3/2004 | Martin et al. |
| 2004/0059328 A1 | 3/2004 | Daniel et al. |
| 2004/0087936 A1 | 5/2004 | Stern et al. |
| 2004/0087994 A1 | 5/2004 | Suddaby |
| 2004/0092946 A1 | 5/2004 | Bagga et al. |
| 2004/0097612 A1 | 5/2004 | Rosenberg et al. |
| 2004/0111136 A1 | 6/2004 | Sharkey et al. |
| 2004/0127987 A1 | 7/2004 | Evans et al. |
| 2004/0133208 A1 | 7/2004 | Weikel et al. |
| 2004/0138758 A1 | 7/2004 | Evans et al. |
| 2004/0153064 A1 | 8/2004 | Foley et al. |
| 2004/0153115 A1 | 8/2004 | Reiley et al. |
| 2004/0158237 A1 | 8/2004 | Abboud et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0210231 A1 | 10/2004 | Broucher et al. |
| 2004/0215343 A1 | 10/2004 | Hochschuler et al. |
| 2004/0220577 A1 | 11/2004 | Cragg |
| 2004/0220680 A1 | 11/2004 | Yamamoto et al. |
| 2004/0225296 A1 | 11/2004 | Reiss et al. |
| 2004/0226479 A1 | 11/2004 | Lyles et al. |
| 2004/0230309 A1 | 11/2004 | DiMauro et al. |
| 2004/0236186 A1 | 11/2004 | Chu |
| 2004/0247644 A1 | 12/2004 | Bratt et al. |
| 2004/0267271 A9 | 12/2004 | Scribner et al. |
| 2005/0027245 A1 | 2/2005 | Sachdeva et al. |
| 2005/0033303 A1 | 2/2005 | Chappuis et al. |
| 2005/0038383 A1 | 2/2005 | Kelley et al. |
| 2005/0038422 A1 | 2/2005 | Maurice |
| 2005/0043737 A1 | 2/2005 | Reiley et al. |
| 2005/0055030 A1 | 3/2005 | Falahee |
| 2005/0060030 A1 | 3/2005 | Lashinski et al. |
| 2005/0070844 A1 | 3/2005 | Chow et al. |
| 2005/0070912 A1 | 3/2005 | Voellmicke |
| 2005/0070915 A1 | 3/2005 | Mazzuca et al. |
| 2005/0090852 A1 | 4/2005 | Layne et al. |
| 2005/0113836 A1 | 5/2005 | Lozier et al. |
| 2005/0119650 A1 | 6/2005 | Sanders et al. |
| 2005/0124989 A1 | 6/2005 | Suddaby |
| 2005/0143827 A1 | 6/2005 | Globerman et al. |
| 2005/0177168 A1 | 8/2005 | Brunnett et al. |
| 2005/0177210 A1 | 8/2005 | Lueng et al. |
| 2005/0182412 A1 | 8/2005 | Johnson et al. |
| 2005/0182413 A1 | 8/2005 | Johnson et al. |
| 2005/0187556 A1 | 8/2005 | Stack et al. |
| 2005/0199156 A1 | 9/2005 | Khairoun et al. |
| 2005/0209557 A1 | 9/2005 | Carroll et al. |
| 2005/0216018 A1 | 9/2005 | Sennett |
| 2005/0228391 A1 | 10/2005 | Levy et al. |
| 2005/0234425 A1 | 10/2005 | Miller et al. |
| 2005/0240193 A1 | 10/2005 | Layne et al. |
| 2005/0251266 A1 | 11/2005 | Maspero et al. |
| 2005/0251267 A1 | 11/2005 | Winterbottom et al. |
| 2005/0261683 A1 | 11/2005 | Veldhuizen et al. |
| 2005/0283148 A1 | 12/2005 | Janssen |
| 2005/0287771 A1 | 12/2005 | Seamons et al. |
| 2006/0024348 A1 | 2/2006 | Engqvist et al. |
| 2006/0025763 A1 | 2/2006 | Nelson et al. |
| 2006/0041033 A1 | 2/2006 | Bisig et al. |
| 2006/0052743 A1 | 3/2006 | Reynolds |
| 2006/0064101 A1 | 3/2006 | Arramon |
| 2006/0074433 A1 | 4/2006 | McGill et al. |
| 2006/0084977 A1 | 4/2006 | Lieberman |
| 2006/0085009 A1 | 4/2006 | Truckai et al. |

(56) References Cited

U.S. PATENT DOCUMENTS

| | | |
|---|---|---|
| 2006/0100635 A1 | 5/2006 | Reiley et al. |
| 2006/0100706 A1 | 5/2006 | Shadduck et al. |
| 2006/0106392 A1 | 5/2006 | Embry |
| 2006/0106459 A1 | 5/2006 | Truckai et al. |
| 2006/0116689 A1 | 6/2006 | Albans et al. |
| 2006/0116690 A1 | 6/2006 | Pagano |
| 2006/0122623 A1 | 6/2006 | Truckai et al. |
| 2006/0142732 A1 | 6/2006 | Karmarkar et al. |
| 2006/0149268 A1 | 7/2006 | Truckai et al. |
| 2006/0149281 A1 | 7/2006 | Reiley et al. |
| 2006/0156959 A1 | 7/2006 | Engqvist et al. |
| 2006/0184106 A1 | 8/2006 | McDaniel et al. |
| 2006/0184192 A1 | 8/2006 | Markworth et al. |
| 2006/0200121 A1 | 9/2006 | Mowery |
| 2006/0206116 A1 | 9/2006 | Yeung |
| 2006/0206136 A1 | 9/2006 | Sachdeva et al. |
| 2006/0217704 A1 | 9/2006 | Cockburn et al. |
| 2006/0217736 A1 | 9/2006 | Kaneko |
| 2006/0229625 A1 | 10/2006 | Truckai et al. |
| 2006/0229631 A1 | 10/2006 | Reiley et al. |
| 2006/0235417 A1 | 10/2006 | Sala |
| 2006/0259023 A1 | 11/2006 | Abboud et al. |
| 2006/0264819 A1 | 11/2006 | Fischer et al. |
| 2006/0264945 A1 | 11/2006 | Edidin et al. |
| 2006/0266372 A1 | 11/2006 | Miller et al. |
| 2006/0270750 A1 | 11/2006 | Almen et al. |
| 2006/0271061 A1 | 11/2006 | Beyar et al. |
| 2006/0276797 A1 | 12/2006 | Botimer |
| 2006/0276819 A1 | 12/2006 | Osorio et al. |
| 2006/0293687 A1 | 12/2006 | Bogert |
| 2007/0006692 A1 | 1/2007 | Phan |
| 2007/0010845 A1 | 1/2007 | Gong et al. |
| 2007/0016130 A1 | 1/2007 | Leeflang et al. |
| 2007/0016211 A1 | 1/2007 | Botimer |
| 2007/0021769 A1 | 1/2007 | Scribner et al. |
| 2007/0043373 A1 | 2/2007 | Sala |
| 2007/0055201 A1 | 3/2007 | Seto et al. |
| 2007/0055260 A1 | 3/2007 | Cragg |
| 2007/0055266 A1 | 3/2007 | Osorio et al. |
| 2007/0055275 A1 | 3/2007 | Schaller |
| 2007/0055277 A1 | 3/2007 | Osorio et al. |
| 2007/0055278 A1 | 3/2007 | Osorio et al. |
| 2007/0055279 A1 | 3/2007 | Sand et al. |
| 2007/0055281 A1 | 3/2007 | Osorio et al. |
| 2007/0055283 A1 | 3/2007 | Scribner |
| 2007/0055284 A1 | 3/2007 | Osorio |
| 2007/0055285 A1 | 3/2007 | Osorio et al. |
| 2007/0055300 A1 | 3/2007 | Osorio et al. |
| 2007/0055382 A1 | 3/2007 | Osorio et al. |
| 2007/0059281 A1 | 3/2007 | Moseley et al. |
| 2007/0067034 A1 | 3/2007 | Chirico et al. |
| 2007/0093840 A1 | 4/2007 | Pacelli |
| 2007/0114248 A1 | 5/2007 | Kovac |
| 2007/0118142 A1 | 5/2007 | Krueger et al. |
| 2007/0118143 A1 | 5/2007 | Ralph et al. |
| 2007/0142842 A1 | 6/2007 | Krueger et al. |
| 2007/0156130 A1 | 7/2007 | Thistle |
| 2007/0162042 A1 | 7/2007 | Dunker |
| 2007/0173939 A1 | 7/2007 | Kim et al. |
| 2007/0185231 A1 | 8/2007 | Liu et al. |
| 2007/0197935 A1 | 8/2007 | Reiley |
| 2007/0198023 A1 | 8/2007 | Sand et al. |
| 2007/0211563 A1 | 9/2007 | Devries |
| 2007/0233146 A1 | 10/2007 | Henniges et al. |
| 2007/0260223 A1 | 11/2007 | Scheibe et al. |
| 2007/0260257 A1 | 11/2007 | Phan |
| 2007/0270876 A1 | 11/2007 | Kuo et al. |
| 2007/0276319 A1 | 11/2007 | Betts |
| 2007/0282305 A1 | 12/2007 | Goldfarb et al. |
| 2008/0004615 A1 | 1/2008 | Woloszko et al. |
| 2008/0033422 A1 | 2/2008 | Turner et al. |
| 2008/0058725 A1 | 3/2008 | Scribner et al. |
| 2008/0058821 A1 | 3/2008 | Maurer et al. |
| 2008/0058827 A1 | 3/2008 | Osorio et al. |
| 2008/0058840 A1 | 3/2008 | Albrecht |
| 2008/0065020 A1 | 3/2008 | Ralph et al. |
| 2008/0065087 A1 | 3/2008 | Osorio et al. |
| 2008/0065190 A1 | 3/2008 | Osorio et al. |
| 2008/0086142 A1 | 4/2008 | Kohm et al. |
| 2008/0140079 A1 | 6/2008 | Osorio et al. |
| 2008/0183165 A1 | 7/2008 | Buysee et al. |
| 2008/0183265 A1 | 7/2008 | Bly |
| 2008/0195112 A1 | 8/2008 | Liu et al. |
| 2008/0208255 A1 | 8/2008 | Siegal |
| 2008/0221608 A1 | 9/2008 | Betts |
| 2008/0228192 A1 | 9/2008 | Beyer et al. |
| 2008/0249481 A1 | 10/2008 | Crainich |
| 2008/0249525 A1 | 10/2008 | Lee et al. |
| 2008/0255571 A1 | 10/2008 | Truckai et al. |
| 2008/0269766 A1 | 10/2008 | Justis |
| 2008/0269796 A1 | 10/2008 | Reiley et al. |
| 2008/0287741 A1 | 11/2008 | Ostrovsky et al. |
| 2008/0294167 A1 | 11/2008 | Schumacher et al. |
| 2009/0076517 A1 | 3/2009 | Reiley et al. |
| 2009/0105775 A1 | 4/2009 | Mitchell et al. |
| 2009/0131867 A1 | 5/2009 | Liu et al. |
| 2009/0131886 A1 | 5/2009 | Liu et al. |
| 2009/0131945 A1 | 5/2009 | Liu et al. |
| 2009/0131948 A1 | 5/2009 | Liu et al. |
| 2009/0131950 A1 | 5/2009 | Liu et al. |
| 2009/0131986 A1 | 5/2009 | Lee |
| 2009/0182427 A1 | 7/2009 | Liu et al. |
| 2009/0198243 A1 | 8/2009 | Melsheimer |
| 2009/0264862 A1 | 10/2009 | Neidert et al. |
| 2009/0264892 A1 | 10/2009 | Beyar et al. |
| 2009/0292289 A9 | 11/2009 | Sand et al. |
| 2009/0293687 A1 | 12/2009 | Nino et al. |
| 2009/0299282 A1 | 12/2009 | Lau et al. |
| 2010/0057087 A1 | 3/2010 | Cha |
| 2010/0082033 A1 | 4/2010 | Germain |
| 2010/0114184 A1 | 5/2010 | Degtyar |
| 2010/0121332 A1 | 5/2010 | Crainich et al. |
| 2010/0152724 A1 | 6/2010 | Marion et al. |
| 2010/0160922 A1 | 6/2010 | Liu et al. |
| 2010/0211076 A1 | 8/2010 | Germain et al. |
| 2010/0274270 A1 | 10/2010 | Patel |
| 2010/0298832 A1* | 11/2010 | Lau .................... A61B 17/1642 606/80 |
| 2011/0034884 A9 | 2/2011 | Pellegrino et al. |
| 2011/0098701 A1 | 4/2011 | McIntyre et al. |
| 2011/0160737 A1 | 6/2011 | Steffen et al. |
| 2011/0251615 A1 | 10/2011 | Truckai et al. |
| 2011/0295261 A1 | 12/2011 | Germain |
| 2011/0295262 A1 | 12/2011 | Germain et al. |
| 2011/0301590 A1 | 12/2011 | Podhajsky et al. |
| 2012/0065543 A1 | 3/2012 | Ireland |
| 2012/0130381 A1 | 5/2012 | Germain |
| 2012/0158004 A1 | 6/2012 | Burger et al. |
| 2012/0191095 A1 | 7/2012 | Burger et al. |
| 2012/0239049 A1 | 9/2012 | Truckai |
| 2012/0265186 A1 | 10/2012 | Burger et al. |
| 2012/0277730 A1 | 11/2012 | Salahieh |
| 2012/0330180 A1 | 12/2012 | Pellegrino et al. |
| 2012/0330301 A1 | 12/2012 | Pellegrino et al. |
| 2013/0006232 A1 | 1/2013 | Pellegrino |
| 2013/0072941 A1 | 3/2013 | Tan-Malecki et al. |
| 2013/0041377 A1 | 4/2013 | Kuntz |
| 2013/0231654 A1 | 9/2013 | Germain |
| 2013/0237795 A1 | 9/2013 | Carr |
| 2013/0261615 A1 | 10/2013 | Kramer et al. |
| 2013/0261621 A1 | 10/2013 | Kramer et al. |
| 2013/0345709 A1 | 12/2013 | Burger et al. |
| 2014/0135779 A1 | 5/2014 | Germain |
| 2014/0163566 A1 | 6/2014 | Phan et al. |
| 2014/0316413 A1 | 10/2014 | Burger et al. |
| 2014/0350542 A1 | 11/2014 | Kramer et al. |
| 2014/0371740 A1 | 12/2014 | Germain et al. |
| 2015/0216594 A1 | 8/2015 | Prakash |
| 2015/0297246 A1 | 10/2015 | Patel et al. |

(56) References Cited

U.S. PATENT DOCUMENTS

| | | | |
|---|---|---|---|
| 2015/0313614 A1 | 11/2015 | Germain | |
| 2016/0228131 A1 | 8/2016 | Brockman et al. | |

FOREIGN PATENT DOCUMENTS

| CN | 2841051 | 11/2006 |
|---|---|---|
| EP | 1459691 | 9/2004 |
| JP | 2004242936 | 9/2004 |
| JP | 2008510530 | 4/2008 |
| JP | 2008528081 | 7/2008 |
| JP | 2008541878 | 11/2008 |
| JP | 2010063887 | 3/2010 |
| JP | 2011500156 | 1/2011 |
| WO | 1993004634 | 3/1993 |
| WO | 1996013297 | 5/1996 |
| WO | 1996020752 | 7/1996 |
| WO | 1997003611 | 2/1997 |
| WO | 2002003870 | 1/2002 |
| WO | 20113101308 | 12/2003 |
| WO | 2005122938 | 12/2005 |
| WO | 2007036815 | 4/2007 |
| WO | 2007087400 | 8/2007 |
| WO | 2008076330 | 6/2008 |
| WO | 2008084479 | 7/2008 |
| WO | 2010039894 | 4/2010 |
| WO | 2010081187 | 7/2010 |
| WO | 2010135602 | 11/2010 |
| WO | 2010135606 | 11/2010 |
| WO | 2011066465 | 6/2011 |
| WO | 2011114602 | 9/2011 |
| WO | 2011137357 | 11/2011 |
| WO | 2011137377 | 11/2011 |
| WO | 2012071464 | 5/2012 |
| WO | 2013147990 | 10/2013 |
| WO | 2014093673 | 6/2014 |

OTHER PUBLICATIONS

Office Action dated May 1, 2009 for U.S. Appl. No, 12/261,987.
Office Action dated Apr. 26, 2010 for U.S. Appl. No. 12/029,428.
Office Action dated Apr. 24, 2017 for U.S. Appl. No. 14/453,427.
European Examination Report dated Dec. 19, 2017 for EP13767383.6.
European Search Report dated Jan. 7, 2019 for EP16793433.0.
European Search Report dated Jun. 8, 2017 for EP17154660.9.
European Search Report dated Nov. 15, 2017 for EP09818476.5.
European Search Report dated Nov. 16, 2016 for EP14772615.2.
International Search Report and Written Opinion dated Jan. 9, 2012 for PCT/US2011/034185.
International Search Report and Written Opinion dated Jan. 22, 2009 for PCT/US2008/83698.
International Search Report and Written Opinion dated Feb. 21, 2018 for PCT/US2017/063281.
International Search Report and Written Opinion dated Mar. 30, 2018 for PCT/US2017/065328.
International Search Report arid Written Opinion dated Apr. 23, 2016 for PCT/US2018/012372.
International Search Report and Written Opinion dated Jul. 20, 2010 for PCT/US2010/035687.
International Search Report and Written Opinion dated Jul. 26, 2011 for PCT/US2011/034628.
International Search Report and Written Opinion dated Aug. 25, 2009 for PCT/US2009/035726.
International Search Report and Written Opinion dated Nov. 20, 2009 for PCT/US2009/059113.
Notice of Allowance dated Jan. 4, 2017 for U.S. Appl. No. 13/302,927.
Notice of Allowance dated Jan. 18, 2017 for U.S. Appl. No. 13/097,998.
Notice of Allowance dated Feb. 21, 2019 for U.S. Appl. No. 14/139,372.
Notice of Allowance dated Apr. 3, 2019 for U.S. Appl. No. 15/349,715.
Notice of Allowance dated Apr. 9, 2014 for U.S. Appl. No. 12/578,455.
Notice of Allowance dated Apr. 23, 2018 for U.S. Appl. No. 13/083,411.
Notice of Allowance dated May 3, 2017 for U.S. Appl. No. 14/815,620.
Notice of Allowance dated May 11, 2018 for U.S. Appl. No. 14/453,427.
Notice of Allowance dated May 26, 2015 for U.S. Appl. No. 13/098,116.
Notice of Allowance dated Aug. 24, 2018 for U.S. Appl. No. 15/388,598.
Notice of Allowance dated Oct. 28, 2016 for U.S. Appl. No. 13/853,397.
Notice of Allowance dated Nov. 8, 2013 for U.S. Appl. No. 12/578,455.
Notice of Allowance dated Nov. 9, 2017 for U.S. Appl. No. 14/815,812.
Notice of Allowance dated Nov. 18, 2016 for U.S. Appl. No. 13/097,998.
Notice of Allowance dated Nov. 25, 2013 for U.S. Appl. No. 12/571,174.
Notice of Allowance dated Nov. 25, 2016 for U.S. Appl. No. 13/853,397.
Notice of Allowance dated Dec. 13, 2018 for U.S. Appl. No. 15/917,454.
Notice of Allowance dated Dec. 28, 2017 for U.S. Appl. No. 15/211,359.
Notice of Allowance dated Aug. 31, 2016 for U.S. Appl. No. 14/887,007.
Office Action dated Jan. 18, 2017 for U.S. Appl. No. 14/815,620.
Office Action dated Jan. 26, 2011 for U.S. Appl. No. 11/941,764.
Office Action dated Jan. 26, 2017 for U.S. Appl. No. 14/815,812.
Office Action dated Feb. 3, 2016 for U.S. Appl. No. 13/853,397.
Office Action dated Feb. 10, 2015 for U.S. Appl. No. 13/083,411.
Office Action dated Feb. 23, 2010 for U.S. Appl. No. 11/941,733.
Office Action dated Feb. 23, 2010 for U.S. Appl. No. 11/941,764.
Office Action dated Mar. 1, 2017 for U.S. Appl. No. 15/211,359.
Office Action dated Mar. 21, 2011 for U.S. Appl. No. 11/941,764.
Office Action dated Mar. 21, 2011 for U.S. Appl. No. 12/029,428.
Office Action dated Apr. 19, 2018 for U.S. Appl. No. 15/388,598.
Park, et al., The Materials Properties of Bone-Particle Impregnated PMMA, Journal of Biomedical Engineering, vol. 108 ,1986 ,141-148.
Park, et al., Biornaterials: An Introduction—Second Edition, Plenum Press ,1992 ,177-178.
Liu, et al., Bone-Particle-Impregnated Bone Cement: An In Vitro Study, Journal of Biomedical Materials Research, vol. 21 , 1987 ,247-261.
Office Action dated May 5, 2010 for U.S. Appl. No. 11/941,764.
Office Action dated May 6, 2019 for U.S. Appl. No. 15/675,315.
Office Action dated May 13, 2009 for U.S. Appl. No. 12/029,428.
Office Action dated May 17, 2010 for U.S. Appl. No. 12/261,987.
Office Action dated May 21, 2014 for U.S. Appl. No. 13/098,116.
Office Action dated May 24, 2012 for U.S. Appl. No. 12/578,455.
Office Action dated May 31, 2016 for U.S. Appl. No. 14/815,620.
Office Action dated Jun. 4, 2018 for U.S. Appl. No. 15/349,715.
Office Action dated Jun. 8, 2009 for U.S. Appl. No. 11/941,764.
Office Action dated Jun. 12, 2009 for U.S. Appl. No. 11/941,733.
Office Action dated Jun. 21, 2018 for U.S. Appl. No. 13/215,098.
Office Action dated Jun. 22, 2018 for U.S. Appl. No. 15/917,454.
Office Action dated Jun. 25, 2015 for U.S. Appl. No. 13/853,397.
Office Action dated Jun. 29, 2018 for U.S. Appl. No. 15/449,591.
Office Action dated Jul. 11, 2017 for U.S. Appl. No. 14/815,812.
Office Action dated Jul. 12, 2010 for U.S. Appl. No. 11/941,764.
Office Action dated Jul. 12, 2017 for U.S. Appl. No. 13/083,411.
Office Action dated Jul. 25, 2011 for U.S. Appl. No. 11/941,733.
Office Action dated Jul. 29, 2013 for U.S. Appl. No. 13/098,116.
Office Action dated Jul. 30, 2013 for U.S. Appl. No. 13/083,411.
Office Action dated Sep. 1, 2010 for U.S. Appl. No. 12/029,428.
Office Action dated Sep. 6, 2017 for U.S. Appl. No. 15/211,359.
Office Action dated Sep. 26, 2017 for U.S. Appl. No. 15/388,598.
Office Action dated Oct. 2, 2018 for U.S. Appl. No. 14/139,372.
Office Action dated Oct. 30, 2018 for U.S. Appl. No. 15/349,715.

(56) References Cited

OTHER PUBLICATIONS

Office Action dated Nov. 3, 2008 for U.S. Appl. No. 11/941,764.
Office Action dated Nov. 3, 2008 for U.S. Appl. No. 12/029,428.
Office Action dated Nov. 5, 2008 for U.S. Appl. No. 11/941,733.
Office Action dated Nov. 12, 2013 for U.S. Appl. No. 13/083,411.
Office Action dated Nov. 25, 2016 for U.S. Appl. No. 13/083,411.
Office Action dated Dec. 2, 2009 for U.S. Appl. No. 12/029,428.
Office Action dated Dec. 3, 2012 for U.S. Appl. No. 12/571,174.
Office Action dated Dec. 9, 2009 for U.S. Appl. No. 12/262,064.
Office Action dated Dec. 11, 2009 for U.S. Appl. No. 12/261,987.
Office Action dated Feb. 27, 2013 for U.S. Appl. No. 12/578,455.
Office Action dated Jul. 12, 2016 for U.S. Appl. No. 14/887,007.
Office Action dated Sep. 10, 2013 for U.S. Appl. No. 12/571,174.
Disc-O-Tech confidence Cement System at http://www.disc-o-tech.com/Articles/Article.asp?CategoryID=4&ArticieID=168 accessed, ,Dec. 3, 2007.
Dai, et al., Bone-Particle-Impregnated Bone Cement: an in vivo weight-bearing study, Journal Biomedical Materials Search, vol. 25 ,191 ,141-156.
Hasenwinkel, et al.,"A Novel High-Viscosity, Two-Solution Acrylic Bone Cement: Effect of Chemical Composition on Properties", J. Biomed Mater. Res. vol. 47, No. 1 ,1999 ,36-45.
Klawitter, et al., Application of Porous Ceramics for the Attachment of Load Bearing Internal Orthopedic Applications, J. Biomed. Mater. Res. Symp., 2(1) ,1972 ,61-229.
International Search Report and Written Opinion dated Feb. 7, 2018 for PCT/US2017/058303.
Notice of Allowance dated Aug. 8, 2019 for U.S. Appl. No. 15/836,125.
Notice of Allowance dated Aug. 9, 2019 for U.S. Appl. No. 15/836,241.
Examination Report dated Aug. 23, 2019 for India Application No. 10013/CHENP/2012.

\* cited by examiner

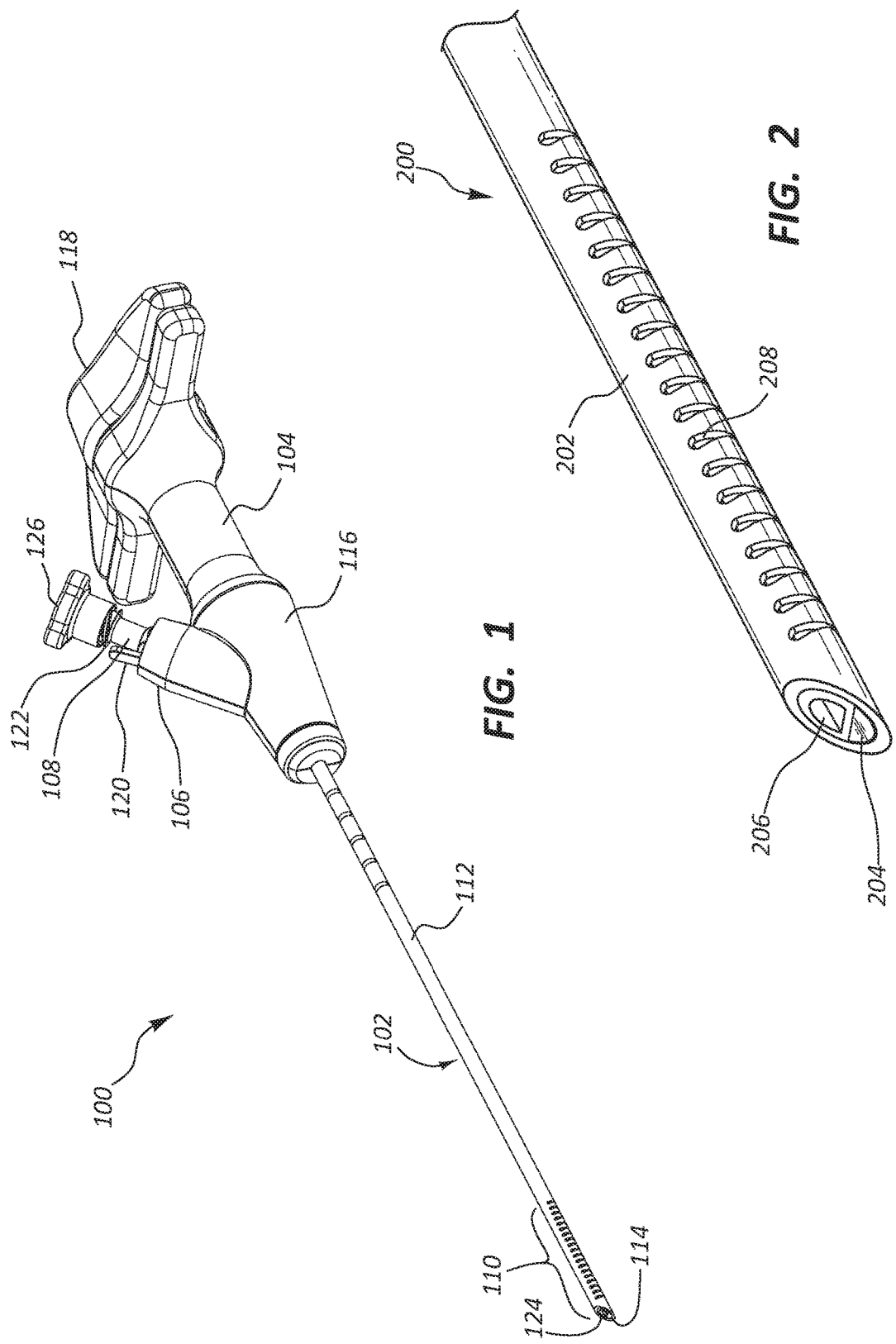

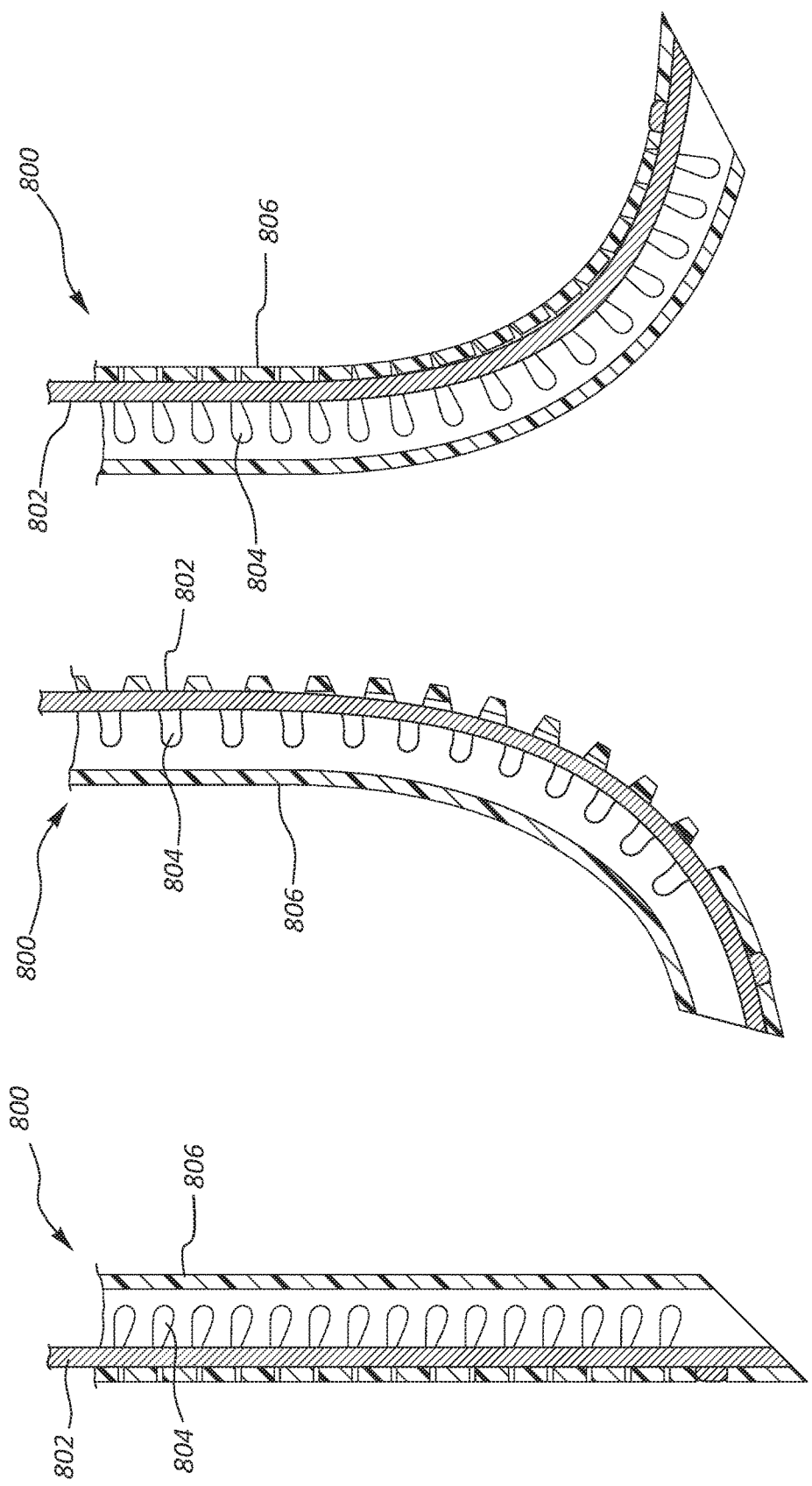

ARTICULATING OSTEOTOME WITH CEMENT DELIVERY CHANNEL

RELATED APPLICATIONS

This application claims priority to U.S. Provisional Application No. 62/413,768, filed on Oct. 27, 2016 and titled, "Articulating Osteotome with Cement Delivery Channel," which is hereby incorporated by reference in its entirety.

TECHNICAL FIELD

The present disclosure relates generally systems and methods for treating bone or hard tissue. More particularly, some embodiments relate to medical instruments and methods for creating a path or cavity in vertebral bone and injecting bone cement to treat a vertebral compression fracture.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 1 is a perspective view of a medical device for treating hard tissue, according to one embodiment.

FIG. 2 is a perspective view of a tip of a medical device for treating hard tissue, according to one embodiment.

FIG. 8 illustrates a cross sectional view of an articulating portion of a shaft in a linear configuration.

FIG. 9 illustrates the articulating portion of FIG. 8 in a first curved configuration.

FIG. 10 illustrates the articulating portion of FIG. 8 in a second curved configuration.

DETAILED DESCRIPTION

Figure 3:
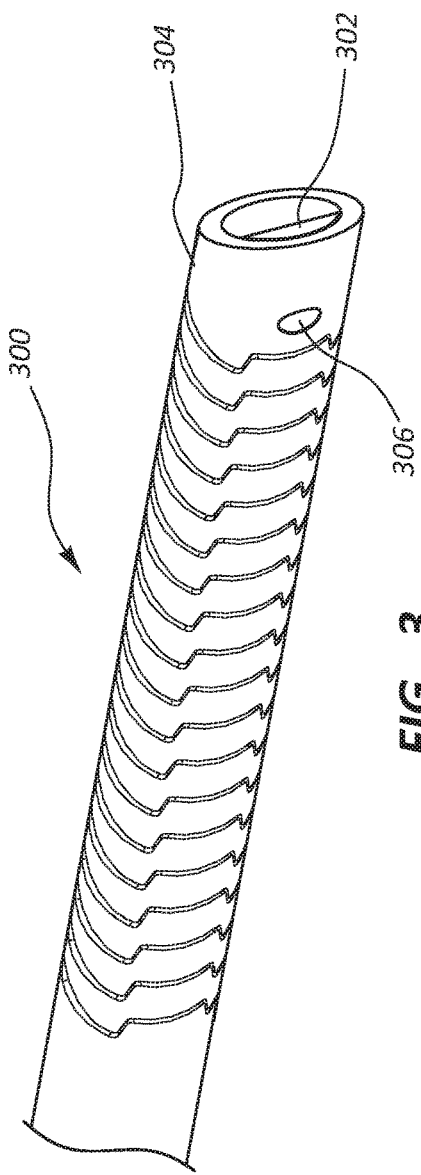
FIG. 3 is a perspective view of an articulating portion of a medical device for treating hard tissue, according to one embodiment.

This disclosure provides methods and systems to treat hard tissue by creating and filling cavities within a bone or other hard tissue. A medical device for treating hard tissue may include a shaft with an articulating portion, a handle configured to manipulate the articulating portion, a side port that extends to an accessible portion of the shaft, and a lumen that is inserted in the side port. In one embodiment, a physician may advance the articulating portion of the shaft into a vertebral body. The physician may manipulate the handle to cause the articulating portion to move from a linear configuration to a non-linear configuration. The change of the articulating portion's configuration may displace tissue in the vertebral body creating a pathway. The physician may inject bone cement through the lumen while the articulating portion is in a non-linear configuration allowing precise filling of the pathway.

The shaft may include a conduit and a rod. The conduit may have a series of slots along a first side of a distal portion. The slots may allow the distal portion to deflect thus forming an articulating distal portion of the conduit. The rod may include a semicylindrical portion that extends through the conduit. The semicylindrical portion's shape may allow the rod to flex when a force is applied and return to a linear position when the force is removed.

The rod may be coupled to the distal end of the conduit. In some embodiments, the rod and the conduit may be directly attached. For example, the rod and conduit may be welded together at the distal end. The weld may be along a distal tip of the rod and the conduit. In some embodiments, the weld may be disposed at an additional notch, hole or slot of the conduit, thereby increasing the welded surface area of the conduit and rod. In other words, the weld joint may be made around the perimeter of the notch hole or slot to attach the rod to the conduit.

The rod may extend through the conduit. The rod may extend along the slots on the first side of the conduit. The position of the slots in the conduit, and the relative position of the rod relative to the conduit, may limit the articulating distal portion to movement in one plane. In some instances, when the rod is translated in the proximal direction (without displacing the conduit), the coupling and the positioning between the rod and the conduit may cause the rod and the conduit to flex at the articulating distal portion.

The shaft may also include a sharp tip located at an end of the articulating distal portion of the conduit to penetrate hard tissue. In some embodiments, the tip may be formed from the conduit and/or rod. In another embodiment, the sharp tip may be a separate part coupled to the conduit and/or rod. The articulating distal portion and tip may have sufficient strength to mechanically displace tissue within a vertebra of a patient.

The handle may include an actuating portion coupled to a proximal end of the rod. The movement of the actuating portion may result in an associated movement of the rod. For example, the actuating portion may control the axial movement of the rod. In some embodiments, rotation of the actuating portion may result in a proximal movement of the rod. Thus, by rotating the an actuating portion a selected amount, the articulating portion can be articulated to a selected degree, and the articulating distal portion may selectively move between a linear configuration and an articulated configuration.

The handle may further include a force limiter. The force limiter may disengage the actuating portion from the proximal end of the rod if a target force is exerted on the actuating portion. The target force may be near the breaking point of the articulating distal portion. The force limiter may protect the articulating distal portion from breaking.

Similarly, in some instances, the entire conduit and rod assembly may be coupled to the handle view a clutch or torque limiting assembly. Such an assembly may limit the amount of torque that can be transferred from the handle to the conduit and rod assembly. This torque limiting assembly can reduce breakage of the rod and/or conduit due to excessive force applied by the handle.

In some embodiments which include a torque limiter, cement or other substances may be displaceable along an injection path through the torque limiter assembly by way of a shuttle component. The shuttle component may be rotationally displaceable with respect to the conduit and may comprise opening around its circumference to create a fluid path regardless of the rotational position of the shuttle with respect to the conduit.

A side port may be coupled to the handle. The side port may have an insertion guide that extends to an accessible portion or working channel the conduit. The working channel or accessible portion of the conduit may be the portion not occupied by the semicylindrical portion of the rod. A lumen may be inserted in the accessible portion.

An inserted lumen may extend through the conduit to an opening in the articulating distal portion. The lumen may be a hollow semicylinder that provides a path for materials to pass through the conduit. The lumen can include a surface comprising a lubricious polymeric material. For example, the material can comprise any bio-compatible material having low frictional properties (e.g., TEFLON®, a polytetrafluoroethylene (PTFE), FEP (Fluorinated ethylenepropylene), polyethylene, polyamide, ECTFE (Ethylenechlorotrifluoroethylene), ETFE, PVDF, polyvinyl chloride and silicone). Similar to the rod, the lumen may be semicylindrical. Semicylindrical rod and the lumen may be positioned within the conduit to form a cylinder that fills the conduit.

A lumen port may be coupled to the lumen. The lumen port may include a clip. The clip may secure the lumen port to a side port with a clip holster. The semicylindrical shape of the rod and the lumen may prevent the lumen from being secured using a threaded connector due to difficulties with rotating a semicylindrical lumen within a semicylindrical accessible portion. The clip provides a method of attachment that will not require the lumen to rotate. The lumen port may selectively couple to a thermal energy delivery probe, a cement delivery cartridge, and a biopsy tool. The lumen may also be selectively removable and replaceable. For example, if cement begins to block the lumen, a new lumen may replace the blocked lumen.

In some embodiments, a stylet may be selectively inserted in the lumen. The stylet may extend through the lumen for additional support to the articulating distal portion. The stylet may be a flexible material that fills the lumen. The stylet may be removed to allow the use of additional tools and cement.

The phrase "coupled to" is broad enough to refer to any suitable coupling or other form of interaction between two or more entities, including mechanical, fluidic and thermal interaction. Thus, two components may be coupled to each other even though they are not in direct contact with each other. The phrases "attached to" or "attached directly to" refer to interaction between two or more entities which are in direct contact with each other and/or are separated from each other only by a fastener of any suitable variety (e.g., mounting hardware or an adhesive). The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms. For example, the distal end of a device or component is the end of the component that is furthest from the physician during ordinary use. The proximal end refers to the opposite end, or the end nearest the physician during ordinary use.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

FIG. 1 is a perspective view of a medical device 100 for treating hard tissue, according to one embodiment. In one embodiment, the medical device 100 may be an osteotome configured for accessing the interior of a vertebral body, creating a pathway in vertebral cancellous bone, and filling the pathway with bone cement. The medical device 100 may include a shaft 102, a handle 104, a side port 106, and a lumen 108.

In use, a physician may introduce the shaft 102 through a pedicle of a patient's spine. The shaft may comprise a conduit 112 and a semicylindrical rod 114. The conduit 112 and rod 114 may be fabricated of a suitable metal alloy, such as stainless steel or NiTi. The shaft may be configured with an articulating portion 110. The articulating portion 110 may deflect along one plane based on the coupling between the conduit 112 and the semicylindrical rod 114. For example, as shown the semicylindrical rod 114 may be contiguous with, and extend along, a series of slots on the conduit 112. The series of slots may allow the conduit 112 to bend and the semicylindrical rod's shape may allow the semicylindrical rod to bend. The articulating portion 110 may be located at the distal end of the shaft.

The articulating portion 110 may progressively actuate to curve a selected degree and/or rotate to create a curved pathway and cavity in the vertebral body. A lumen 108 may be inserted through the side port 106 and extend through the shaft 102 to provide a pathway for bone cement to pass. The articulating portion 110 may remain in a curved state while the bone cement may be injected directly into the cavity.

The handle 104 may be coupled to the proximal end of the shaft 102. The handle 104 may comprise a grip portion 116 and an actuator portion 118. The grip portion 116 may be coupled to the conduit 112. And the actuator portion 118 may be operatively coupled to the semicylindrical rod 114. The shaft 102 may be coupled to the handle 104, to allow a physician to drive the shaft 102 into bone while contemporaneously actuating the articulating portion 110 into an actuated or curved configuration. The handle 104 can be fabricated of a polymer, metal or any other material. In some embodiments, the material of the handle 104 may be suitable to withstand hammering or impact forces used to drive the assembly into bone (e.g., via use of a hammer or similar device on the handle 104).

The actuator portion 118 may be rotatable relative to the grip portion 116. When the actuator portion 118 is turned, the articulating portion 110 may associatively deflect. Some embodiments may have systems or elements for arresting the movement of the actuator portion 118 and thereby maintaining the deflection of the articulating portion 110. For example, in one embodiment, one or more plastic flex tabs of the grip portion may be configured to engage notches in the rotatable actuator portion to provide tactile indication and temporary locking in a certain degree of rotation.

The side port 106 may provide an aperture through the handle 104 into a portion of the shaft 102 not occupied by the semicylindrical rod, the accessible portion or working channel 124. The lumen 108 may be inserted into the side port 106 and extend through the shaft 102 along the working channel 124. The lumen 108 may be secured to the side port 106 with a clip 120. The lumen 108 may further include a threaded port 122 to accept cement delivery devices, biopsy tools, and other medical instruments. In the embodiment illustrated in FIG. 1, a stylet 126 is coupled to the lumen 108 via the threaded port 122, FIG. 2 is a perspective view of a tip 200 of a medical device for treating hard tissue, according to one embodiment. As shown, a conduit 202 may encompass a rod 204 and a lumen 206. The embodiment of the tip 200 shown in FIG. 2 is an example of a tip of the medical device 100 of FIG. 1. In other words, various features of the tip 200 of FIG. 2 may be used in connection with the medical device 100 of FIG. 1 and vice versa. Disclosure recited in connection with FIG. 1 may not be repeated in connection with FIG. 2 but such disclosure analogously applies to the tip 200 of FIG. 2, and vice versa. This pattern of disclosure applies to each figure and embodiment recited in this application, features of each embodiment may be understood as applying analogously to the other embodiments.

The conduit may have a series of slots 208. The notches or slots in any of the sleeves can comprise a uniform width along the length of the working end or can comprise a varying width. Alternatively, the width can be selected in certain areas to effectuate a particular curved profile. In other variations, the width can increase or decrease along the working end to create a curve having a varying radius.

As shown, the rod 204 and the lumen 206 may both be semicylindrical. When paired together, their shape and sizing may form a cylinder that fills the center of the conduit 202. The lumen may provide additional support for the tip 200.

FIG. 3 is a bottom view of an articulating portion 300 of a medical device for treating hard tissue, according to one embodiment. The embodiment of the articulating portion 300 shown in FIG. 3 is an example of a tip of the medical device 100 of FIG. 1. In other words, various features of the articulating portion 300 of FIG. 2 may be used in connection with the medical device 100 of FIG. 1 and vice versa. Disclosure recited in connection with FIG. 1 may not be repeated in connection with FIG. 3 but such disclosure analogously applies to the articulating portion 300 of FIG. 3, and vice versa.

A semicylindrical rod 302 may be attached to a conduit 304 in a variety of ways. For example, the perimeter of the semicylindrical rod's arc may be welded to the conduit 304 at the end. Other attachment spots may be used to secure the semicylindrical rod 302 to the conduit 304. For instance, the weld notch 306 shown provides a welding area to attach the semicylindrical rod 302 to the conduit 304. In some embodiments multiple attachment means may be used to attach the conduit 304 to the semicylindrical rod 302.

Figure 4:
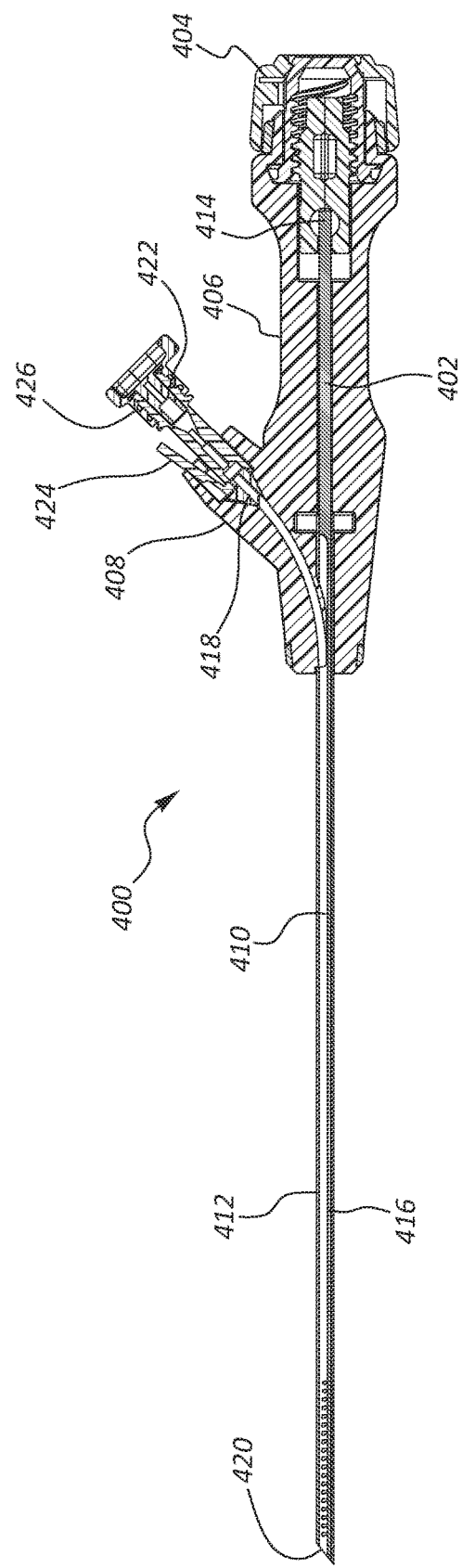
FIG. 4 is a side cross sectional view of a medical device for treating hard tissue, according to one embodiment.

FIG. 4 is a cross sectional view of a medical device 400 for treating hard tissue, according to one embodiment. As shown, the medical device 400 may comprise a rod 402, a handle 406, a side port 408, a lumen 410, and a conduit 412. This cross sectional view of a medical device 400 is an example of the medical device 100 of FIG. 1. In other words, various features of the medical device 400 of FIG. 4 may be used in connection with the medical device 100 of FIG. 1 and vice versa. Disclosure recited in connection with FIG. 1 may not be repeated in connection with FIG. 4 but such disclosure analogously applies to the medical device 400 of FIG. 4, and vice versa.

The rod 402 may comprise a cylindrical proximal end 414 and a semicylindrical distal end 416. The cylindrical proximal end 414 may mechanically couple to an actuator portion 404 of the handle 406. The mechanical coupling between the actuator portion 404 and the cylindrical proximal end 414 may translate a rotation of the actuator portion 404 to a force along the axis of the rod 402. The semicylindrical distal end 416 may extend through the conduit 412 and occupy a bottom portion of the conduit. The semicylindrical distal end 416 may be flexible as compared to the cylindrical proximal end 414 due to its shape.

The actuator portion 404 may displace the cylindrical proximal end 414. The displacement of the cylindrical proximal end 414 exerts a force on semicylindrical distal end 416. The semicylindrical distal end 416 may be attached to the conduit 412, causing the force on the semicylindrical distal end 416 to bend the rod 402 and the conduit 706.

The lumen 410 may enter the conduit 412 via the side port 408. As shown, the side port 408 may be located on an upper portion of the handle 406. The side port 408 may include an aperture 418 that opens to an upper portion of the conduit 412. A physician may insert the lumen through the aperture 418. The lumen 410 may extend through the conduit 412 such that the side port has a first opening 420 at the distal end of the conduit 412 and a second opening 422 at the side port 408.

In some embodiments, the lumen 410 may be secured to the side port with a clip 424. Due to the semicylindrical shapes of the rod 402 and the lumen 410, a standard threaded securing mechanism may not function properly. For example, in an embodiment where the lumen 410 does not have room to rotate in the conduit 412, a standard threaded securing mechanism would not work. The clip 424 provides an alternative to secure the lumen the side port 408 with no need for the lumen 410 to rotate. The lumen may also include a threaded attachment point 426 to selectively couple to a stylet, a thermal energy delivery probe, a cement delivery cartridge, or a biopsy tool.

Figure 5:
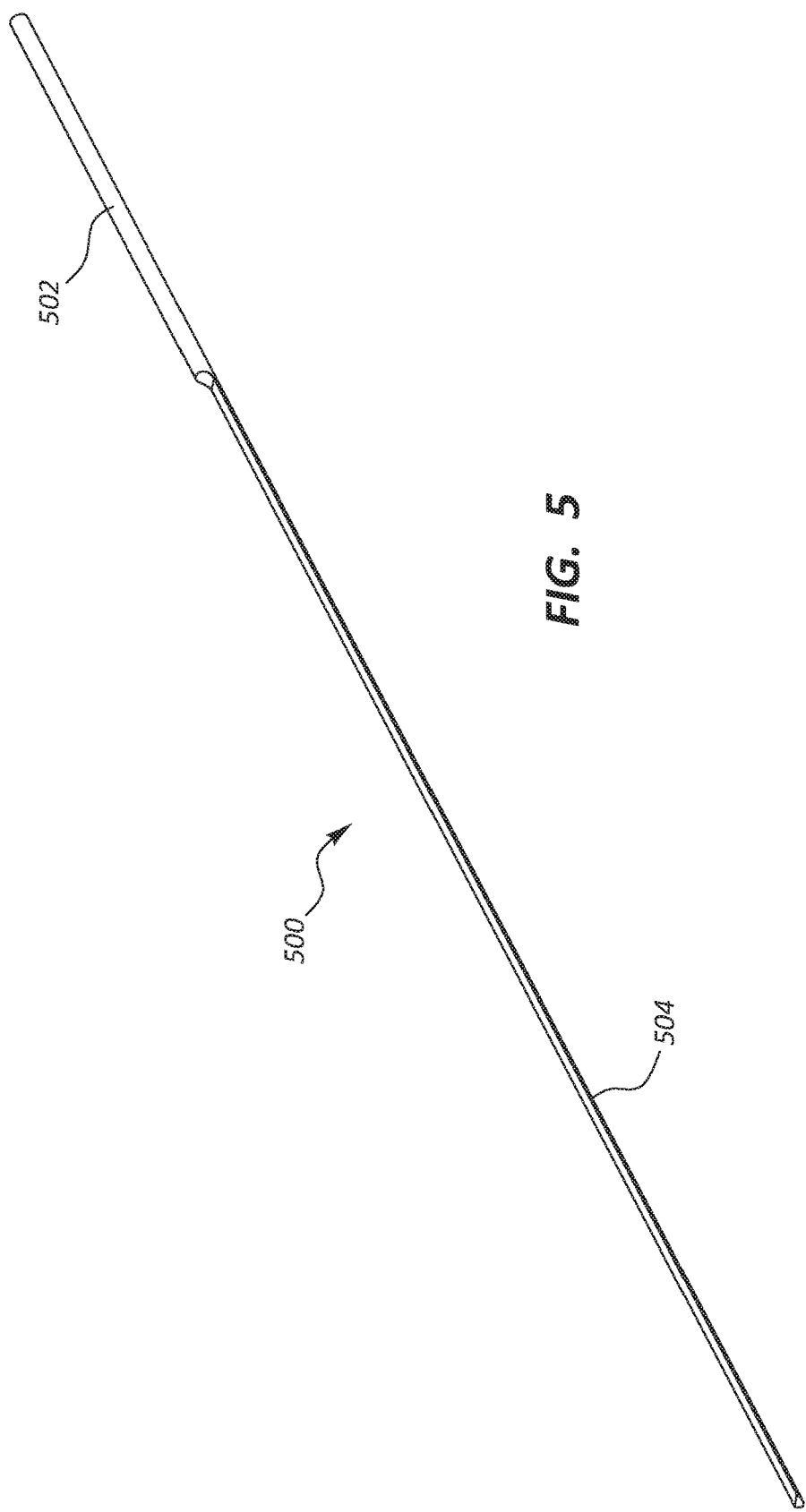
FIG. 5 is a perspective view of an inner rod of a shaft with a semicylindrical portion, according to one embodiment.

FIG. 5 is a perspective view of an inner rod 500 of a shaft. The inner rod 500 of FIG. 5 is an example of the rod 114 in FIG. 1. Disclosure recited in connection with FIG. 1 may not be repeated in connection with FIG. 5 but such disclosure analogously applies to the medical device 500 of FIG. 5, and vice versa.

The inner rod may include a cylindrical portion 502 and a semicylindrical portion 504. The cylindrical portion 502 may provide a rigid length of the inner rod 500 not intended to bend. The semicylindrical portion 504 may be configured via its shape to flex when a force is applied to it. As shown, the narrowing between the cylindrical portion 502 and a semicylindrical portion 504 may be rapid. In an alternative embodiment, the cylindrical portion 502 may gradually narrow to a semicylindrical portion 504 to allow greater flexibility at some points of the inner rod 500 than others.

Figure 6:
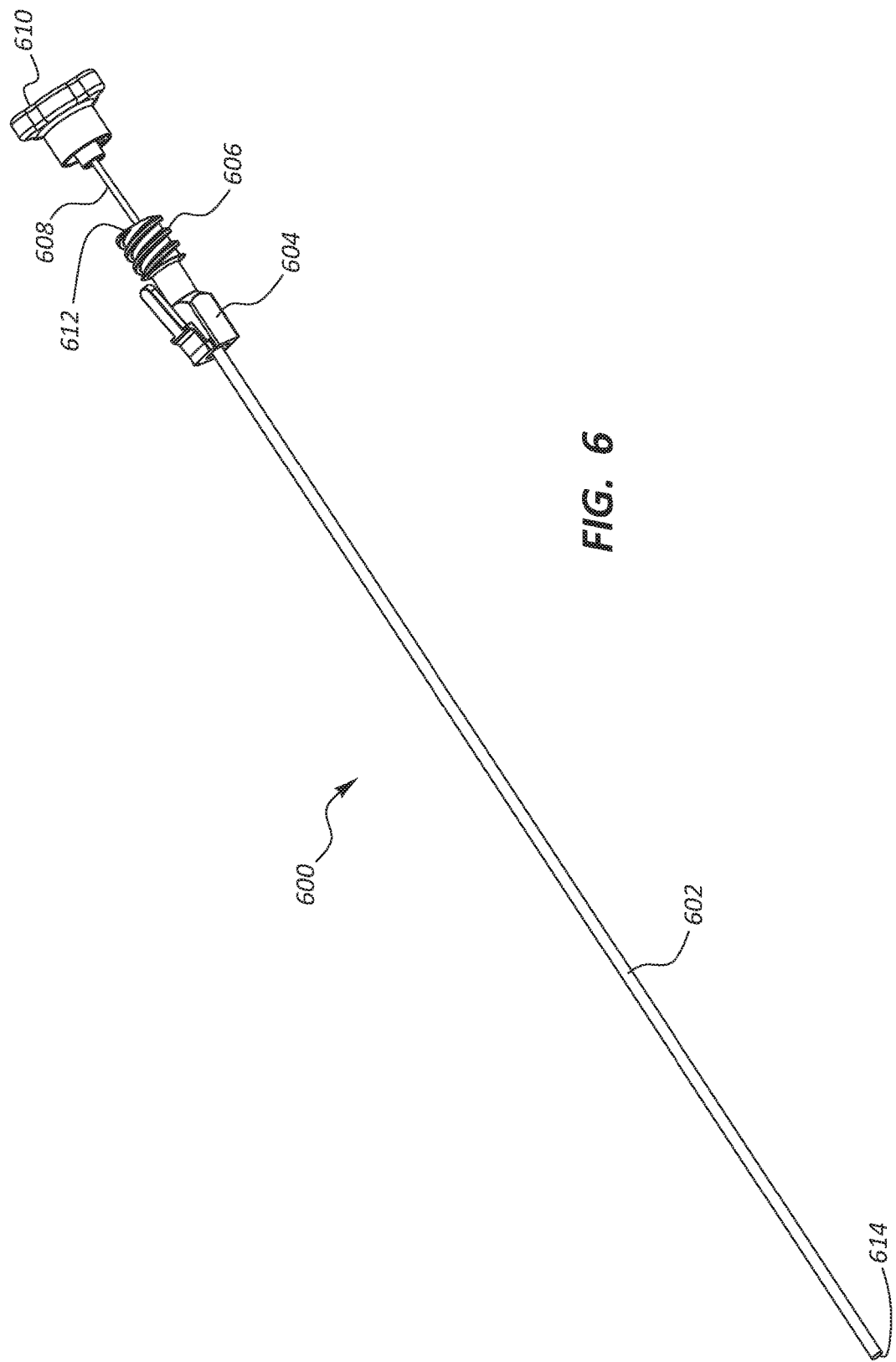
FIG. 6 is a perspective view of a lumen with a stylet, according to one embodiment.

FIG. 6 is a perspective view of a lumen 600 with a stylet 608, according to one embodiment. As shown, the lumen 600 may comprise a liner 602, a side port clip 604, and a threaded mating mechanism 606. The lumen 600 of FIG. 6 is an example of the lumen 108 in FIG. 1. Disclosure recited in connection with FIG. 1 may not be repeated in connection with FIG. 6 but such disclosure analogously applies to the lumen 600 of FIG. 6, and vice versa.

The lumen 600 may provide additional support to a medical device additional strength to treat hard tissue, and allow materials to pass from one end to another end. A first opening 612 may allow materials such as bone cement to enter the lumen 600. A second opening 614 may allow materials that enter into the lumen 600 through the first opening 612 to exit. Alternatively material may be drawn from the second opening 614 out the first opening 612 for procedures such as biopsies. The side port clip 604 may secure the lumen 600 to a medical device, and the threaded mating mechanism 606 may secure the lumen to additional tools such as a thermal energy delivery probe, a cement delivery cartridge, or a biopsy tool.

The stylet may include a cap 610 to secure the stylet 608 to the lumen 600 via the threaded mating mechanism 606. The cap 610 may also prevent foreign material from entering a vertebra through the lumen 600. The stylet 608 may be supportive, such that when a stylet 608 is inserted in the lumen 600, the resulting combination is more rigid than the lumen 600 alone. This may provide a medical device additional strength to treat hard tissue. In some embodiments, a stylet 608 may be very flexible for greater movement of the medical device. In an alternative embodiment, the stylet 608 may be semi-rigid for extra support.

Figure 7:
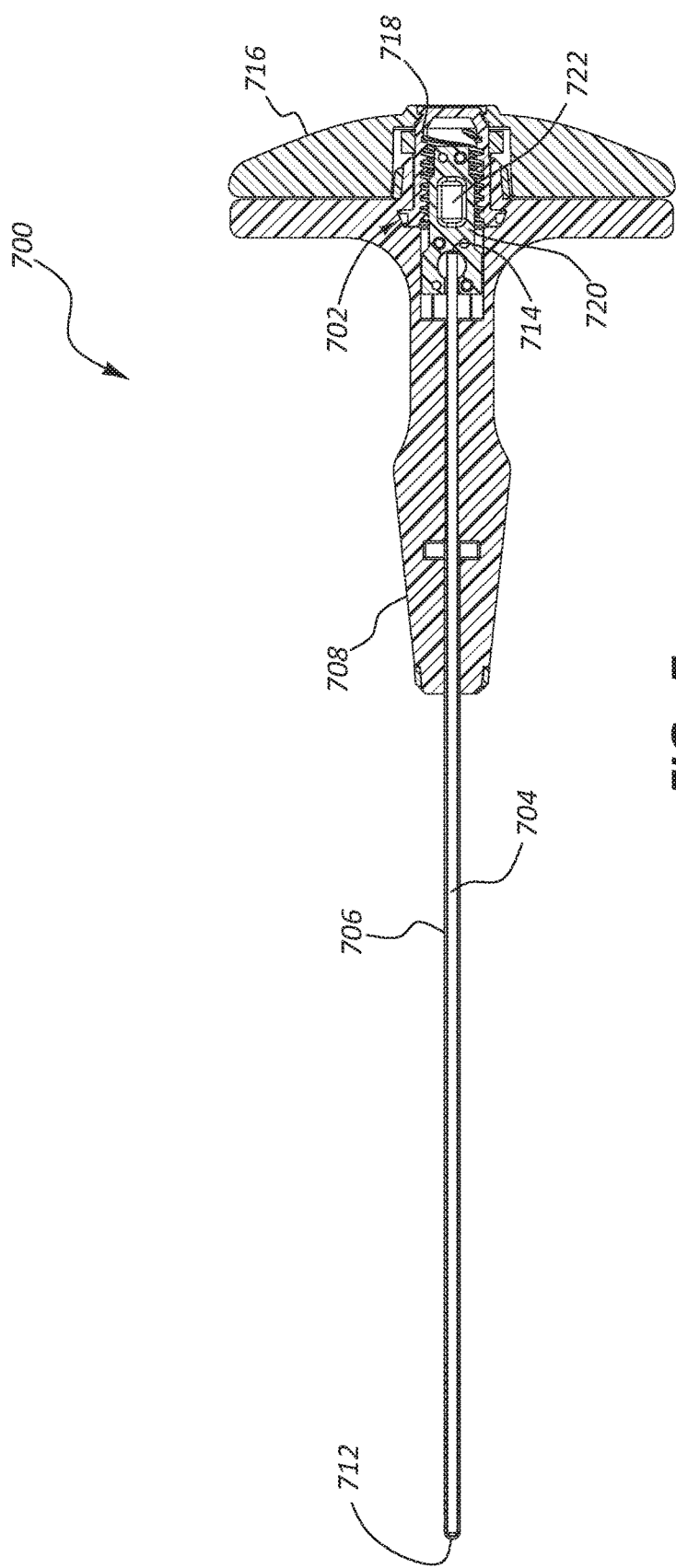
FIG. 7 is a top cross sectional view of a medical device, according to one embodiment.

FIG. 7 is a top cross sectional view of a medical device 700, according to one embodiment. As shown, the medical device 700 may comprise a mechanism for actuating 702 the rod 704 relative to the conduit 706. This top cross sectional view of a medical device 700 is an example of the medical device 100 of FIG. 1. In other words, various features of the medical device 700 of FIG. 7 may be used in connection with the medical device 100 of FIG. 1 and vice versa. This medical device 700 is also an example of the medical device 400 of FIG. 4 with the cross section taken along a different plane. Disclosure recited in connection with FIG. 1 may not be repeated in connection with FIG. 7 but such disclosure analogously applies to the medical device 700 of FIG. 7, and vice versa.

The conduit 706 may be statically attached to the handle 708. In some embodiments, the conduit 706 may be attached to the handle 708 via a weld, O-ring, molding, and/or clamp. The attachment may prevent the conduit 706 from moving or rotating relative to the handle 708. The conduit 706 may also be attached to the rod 704 at or near a distal tip 712, The rod 704 may be attached to the mechanism for actuating 702 at a proximal end. The mechanism for actuating 702 may selectively translate the rod 704 toward or away from the distal tip 712. A translation may cause the rod 704 to push or pull at the attachment point between the conduit 706 and the rod 704. Because the conduit 706 is static relative to the handle, the pushing or pulling may cause the rod 704 and the conduit 706 to deflect.

The mechanism for actuating 702 may be coupled to an actuator portion 716 of a handle. The mechanism for actuating 702 may include a thread actuator 718 and a clam shell 720 with threaded mating bearing 722. The thread actuator 718 may couple to the actuator portion, such that when a physician rotates the actuator portion 716, the thread actuator 718 also rotates. The clam shell 720 may attach to the rod 704 and engage the thread actuator 718 with the threaded mating bearing 722. As the thread actuator 718 rotates, the threaded mating bearing 722 may slide along the threads of the thread actuator 718 preventing the clam shell 720 from rotating while translating the clam shell toward or away from the distal tip 712.

The mechanism for actuating 702 may displace the proximal end of the rod 704. The displacement of the proximal end of the rod 704 exerts a force on the distal end of the rod 704. Because the distal end of the rod 704 is attached to the conduit 706, the force on the distal end of the rod 704 causes the rod 704 and the conduit 706 to flex.

FIGS. 8-10 illustrate cross sectional views of an articulating portion 800 of a shaft in a linear configuration and a first and a second curved configuration. The articulating portion 800 may be analogous to the articulating portion 110 of FIG. 1. The articulating portion 110 of FIG. 1 may operate in analogously to the articulation portion 800 of FIG. 8, and vice versa.

The ability of the articulating portion 800 to curve is due to the notches 804 in the conduit 806 and the shape of the rod 802. The rod's semicylindrical shape causes it to have a greater flexibility than if the rod was cylindrical to permit the rod 802 to bend. The direction the articulating portion 800 may be limited by the location of the notches 804 in conduit 806. For instance, the articulating portion 800 may only bend along the plane of the notches 804. The articulating portion 800 is rigid in any other direction. The curvature of any articulated configuration is controlled by the spacing of the notches as well as the distance between each notch peak.

FIG. 8 illustrates the articulating portion 800 in a linear configuration. FIG. 9 illustrates the articulating portion 800 in a first curved configuration. The first curved configuration is caused when the rod 802 pushes the conduit 806 in the distal direction. For instance, the rod 802 may be welded near the tip to the conduit 806. Because the rod is attached to the conduit, a force pushing the rod 802 while the conduit 806 is held stationary would cause the rod 802 to push the tip of the conduit 806 causing it to flex to allow the rod to move in the distal direction. FIG. 10 illustrates the articulating portion 800 in a second curved configuration. The second curved configuration is caused when the rod 802 pulls the conduit 806 in the proximal direction. For instance, the rod 802 may be welded near the tip to the conduit 806. Because the rod is attached to the conduit, a force pulling the rod 802 while the conduit 806 is held stationary would cause the rod 802 to pull the tip of the conduit 806 causing it to flex to allow the rod to move in the proximal direction.

Figure 11:
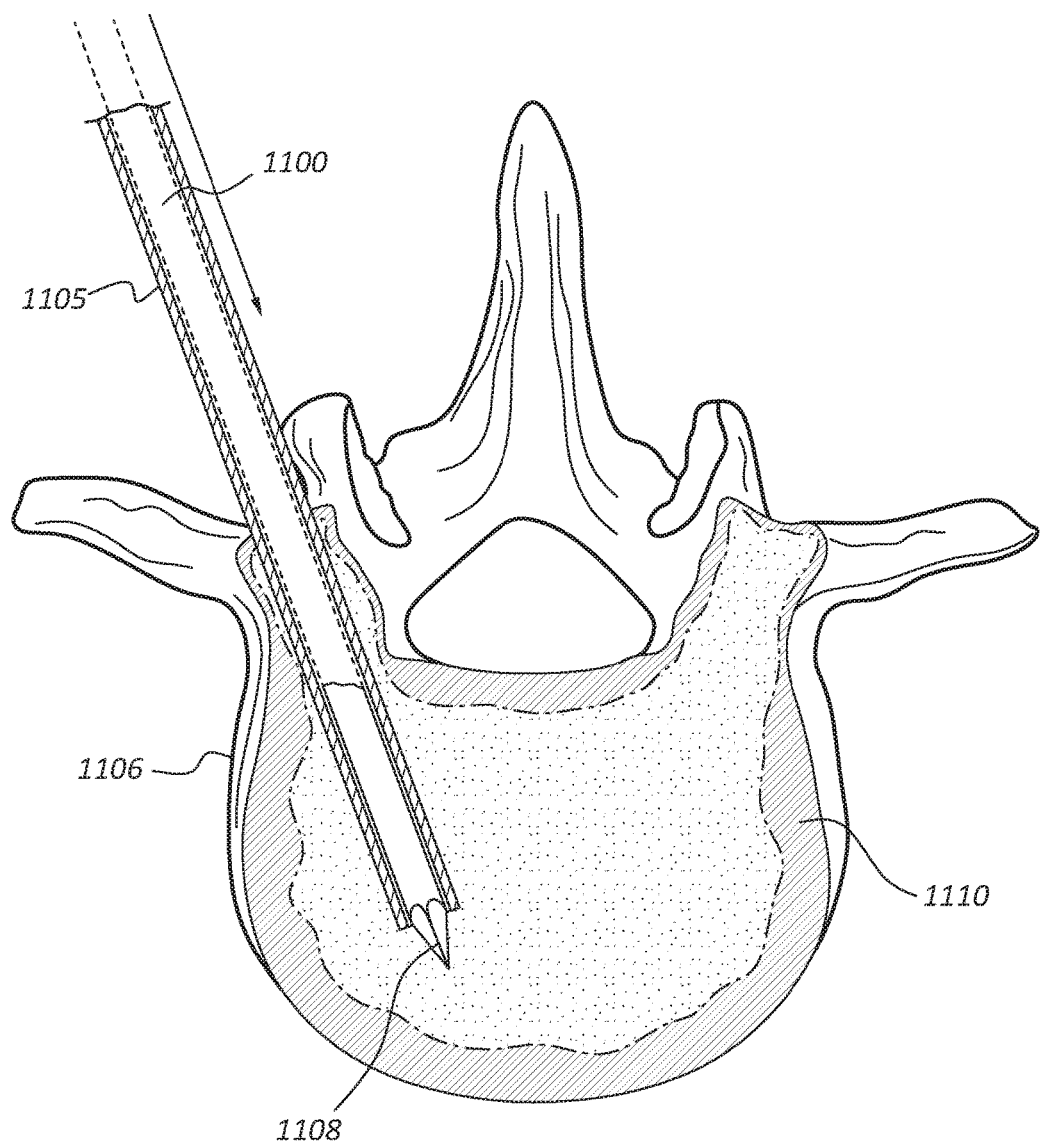
FIG. 11 illustrates an introducer inserted into a vertebral body.
Figure 12:
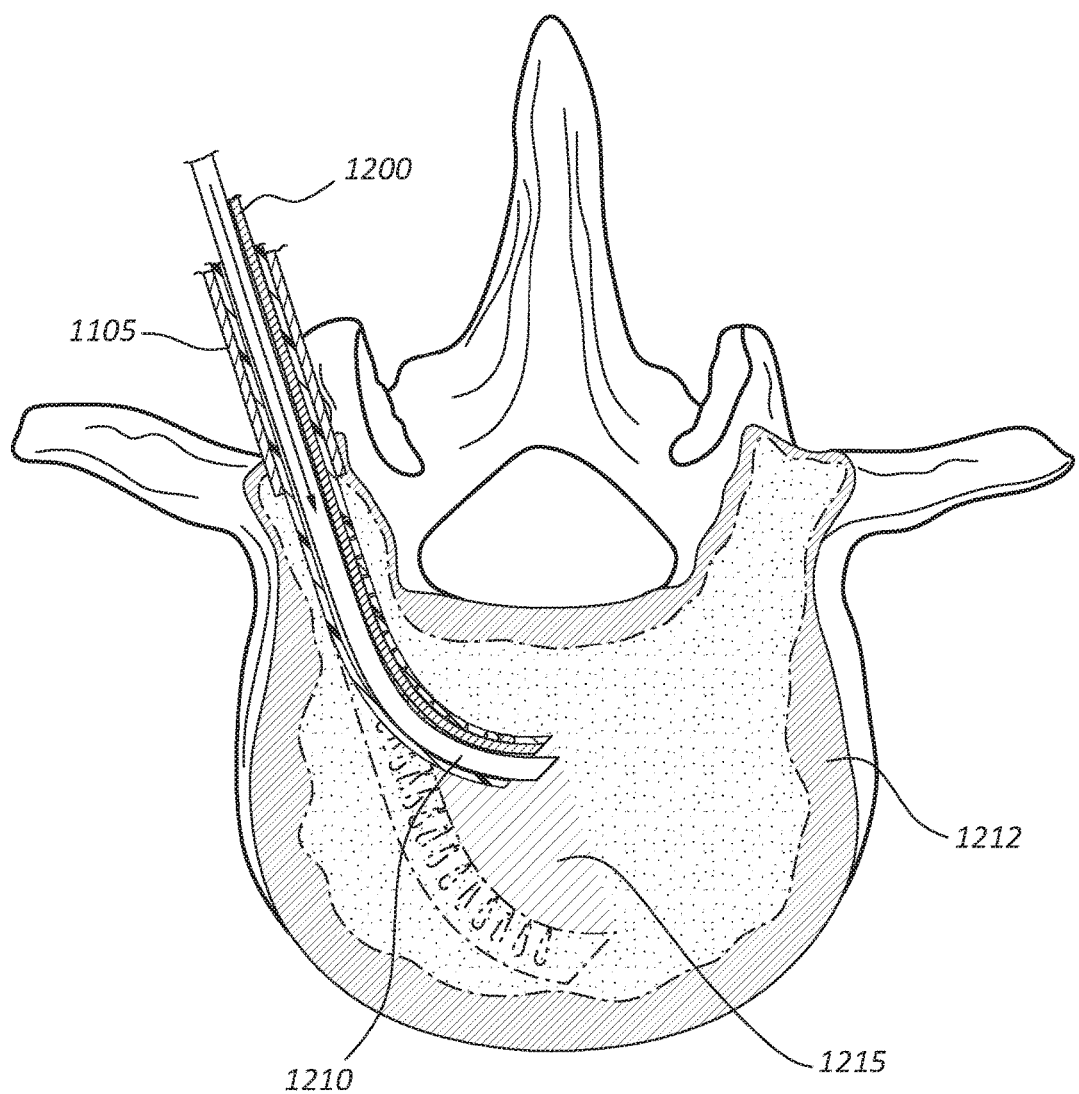
FIG. 12 illustrates an osteotome creating a pathway in the vertebral body of FIG. 11.
Figure 13:
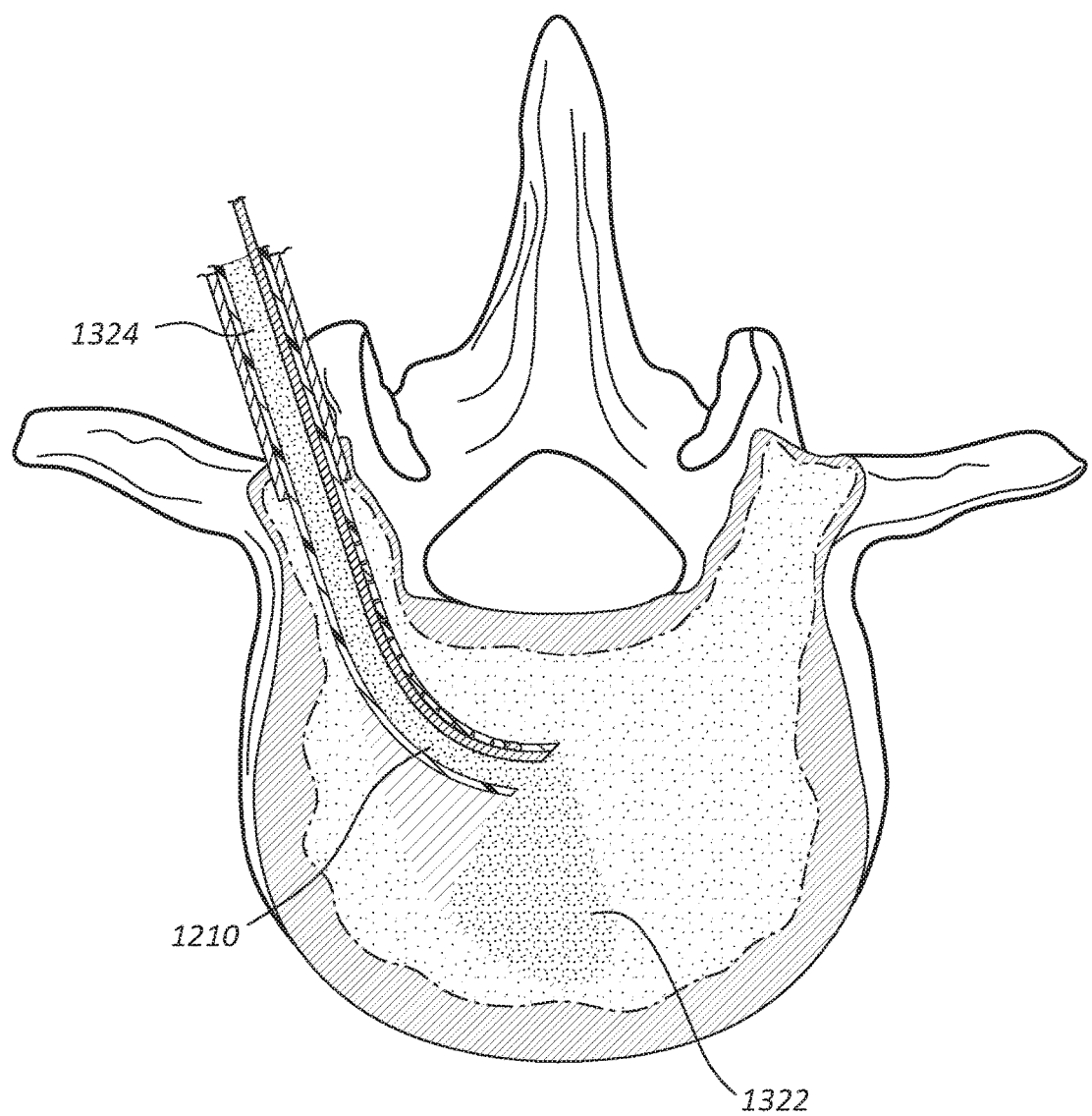
FIG. 13 is a cross sectional view of bone cement being injected into the pathway of FIG. 12 through a lumen in the osteotome.

FIGS. 11-13 are cross sectional views of an osteotome in use, according to one exemplary method. The method may include obtaining a medical device having a sharp tip configured for penetration into vertebral bone, the medical device comprising, advancing the working end into a vertebral body. Once in the vertebral body, the physician may cause the working end to move from a linear configuration to a non-linear to create a pathway in the vertebral body. The physician may further inject a fluid through the lumen while the working end is in a non-linear configuration to fill the pathway with the fluid in a precise pattern.

FIG. 11 illustrates an introducer 1100 being inserted into a vertebral body 1106. A physician taps or otherwise drives an introducer 1100 and sleeve 1105 into a vertebral body 1106 typically until the introducer tip 1108 is within the anterior ⅓ of the vertebral body toward cortical bone 1110.

Thereafter, the introducer 1100 is removed and the sleeve 1105 is moved proximally (FIG. 12). As can be seen in FIG. 12, the tool or osteotome 1200 is inserted through the introducer sleeve 1105 and articulated. The osteotome 1200 may be the medical device 100 in FIG. 1. The working end 1210 can be articulated intermittently while applying driving forces and optionally rotational forces to a handle of the osteotome to advance the working end through the cancellous bone 1212 to create path or cavity 1215. The tool is then tapped to further drive the working end 1210 to, toward or past the midline of the vertebra. The physician can alternatively articulate the working end 1210, and drive and rotate the working end further until imaging shows that the working end 1210 has created a cavity 1215 of an optimal configuration.

Thereafter, as depicted in FIG. 13, the physician may inject bone cement 1322 through a lumen 1324 while the working end 1210 is in a non-linear configuration. The capability of injecting bone cement 1322 while the working end 1210 in a non-linear configuration provides the physician with precise control over how the path or cavity is filled.

Figure 14:
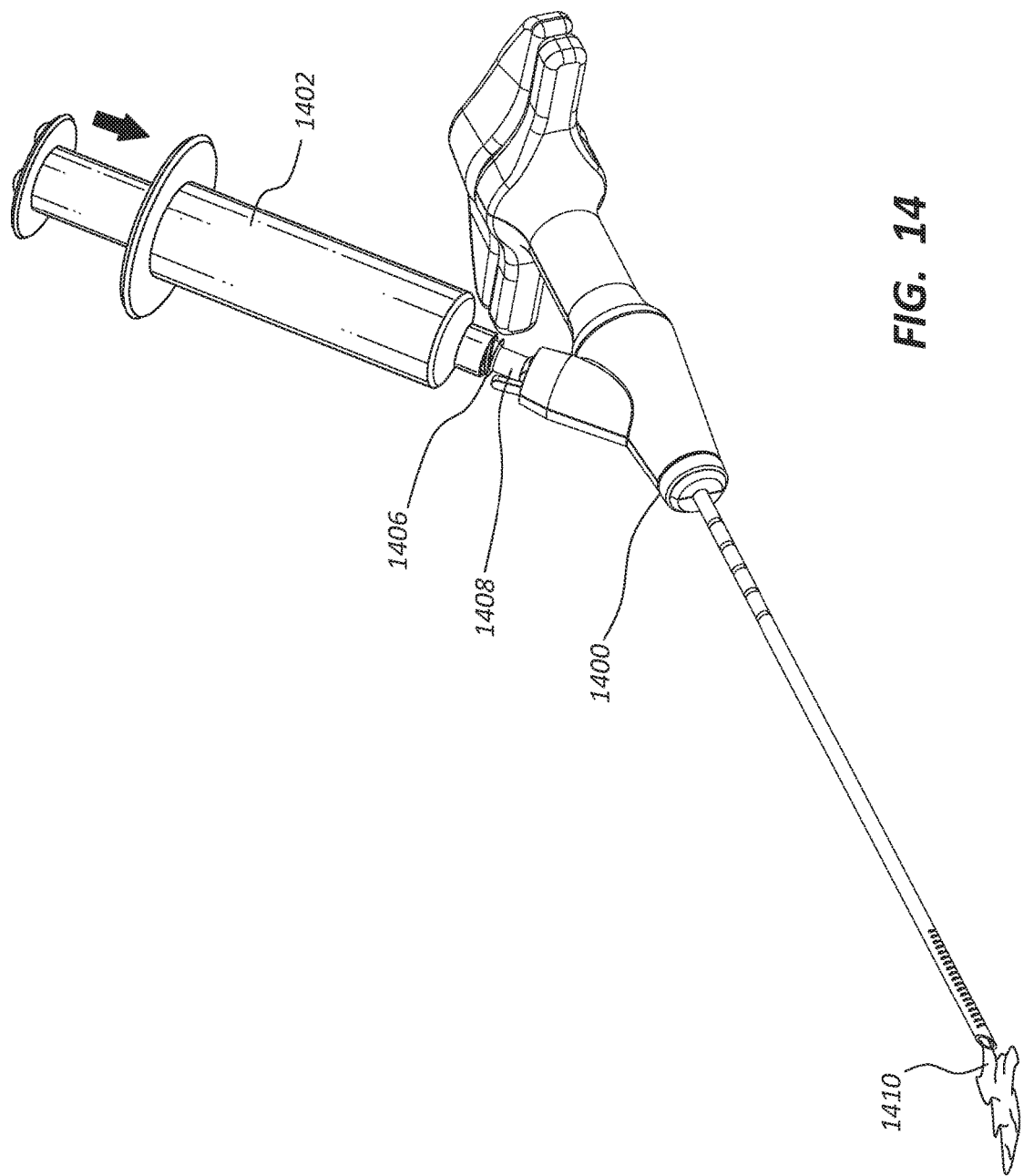
FIG. 14 is a perspective view of a medical device for treating hard tissue fluidly coupled to a bone cement injector, according to one embodiment.

FIG. 14 is a perspective view of a medical device 1400 for treating hard tissue fluidly coupled to a bone cement injector 1402, according to one embodiment. As shown, the injector 1402 may couple to the medical device 1400 by engaging the threaded mating mechanism 1406 of the lumen 1408. A physician may use the injector 1402 to push cement through the lumen 1408. The cement may travel through the medical device 1400 and exit a distal tip 1410.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those of skill in the art, having the benefit of this disclosure, that changes may be made to the details of the above-described embodiments without departing from the underlying principles of the present disclosure.

We claim:

1. A medical device for treating hard tissue, comprising: a conduit having a series of slots along a first side of an articulating distal portion of the conduit; a rod extending through the conduit, the rod including a flexible portion; a handle including an actuating portion coupled to a proximal end of the rod, wherein movement of the actuating portion results in an associated movement of the rod and the conduit to selectively move the articulating distal portion between a linear configuration and an articulated configuration; and a side port coupled to the handle with an insertion guide that extends to an accessible portion of the conduit extending along the conduit to a distal end of the conduit; further comprising a lumen inserted in the insertion guide and extending through the conduit, wherein the lumen is semi-cylindrical, and wherein the semicylindrical flexible portion of the rod and the lumen are positioned within the conduit to form a cylinder that fills the conduit.

2. The medical device of claim 1, further comprising a lumen port with a clip coupled to the lumen, and wherein the side port includes a clip holster to secure the lumen port to the side port.

3. The medical device of claim 2, wherein the lumen port is configured to selectively couple to a thermal energy delivery probe, a cement delivery cartridge, and a biopsy tool.

4. The medical device of claim 2, wherein the lumen is selectively removable and replaceable.

5. The medical device of claim 1, wherein the conduit includes a notch on the first side of the distal portion, wherein the conduit and rod are attached by a weld joint around a perimeter of the notch.

6. The medical device of claim 1, wherein the articulating distal portion has sufficient strength to mechanically displace tissue within a vertebra of a patient.

7. The medical device of claim 1, wherein the articulating distal portion is configured to transition from the linear configuration to the articulated configuration in only a single plane.

8. The medical device of claim 2, further comprising a stylet selectively inserted in the lumen and extending through the lumen for additional support to the articulating distal portion.

9. The medical device of claim 1, wherein the handle further includes a force limiter that disengages the actuating portion from the proximal end of the rod when a target force is exerted on the actuating portion.

10. The medical device of claim 1, wherein the flexible portion comprises a semicylindrical portion coupled to the articulating distal portion of the conduit and contiguous with the first side of the conduit.

11. The medical device of claim 1, further comprising a sharp tip located at an end of the articulating distal portion of the conduit to penetrate hard tissue.

12. A medical device for treating hard tissue within a vertebra of a patient, the medical device comprising:
a shaft having an articulating portion, the shaft comprising:
a hollow conduit with a series of slots along a first side to permit deflection, and
a semicylindrical rod extending through the hollow conduit and contiguous with the first side of the hollow conduit,
wherein the hollow conduit and semicylindrical rod are coupled at a distal end of the articulating portion such that a force applied along an axis of the semicylindrical rod translates to a deflection in the articulating portion to move reversibly between a linear configuration and an articulated configuration, where the series of slots and the semicylindrical rod limit movement between the linear configuration and the articulated configuration to a single plane;
a side port with a clip holster that extends to an accessible portion of the shaft extending along the hollow conduit to a distal end of the conduit; and
a lumen having a clip to selectively secure the lumen to an insertion guide, the lumen extending through the hollow conduit with openings at both ends to permit movement of material through the shaft without being in contact with the shaft.

13. The medical device of claim 12, wherein the articulating portion has sufficient strength to mechanically displace tissue within a vertebra of a patient.

14. The medical device of claim 12, wherein the shaft further comprises a pointed distal end that is configured to penetrate bone within a vertebra of a patient.

15. The medical device of claim 12, wherein the lumen comprises a threaded interface to selectively couple to a thermal energy delivery probe, a cement delivery cartridge, and a biopsy tool.

16. The medical device of claim 12, further comprising a stylet selectively inserted in the lumen and extending through the lumen for additional support to the articulating portion.

17. The medical device of claim 12, further comprising a handle including an actuating portion coupled to a proximal end of the rod, wherein manipulation of the actuating portion causes deflection of the articulating portion.

18. The medical device of claim 17, wherein the handle further includes a force limiter that disengages the actuating portion from the proximal end of the rod when a target force is exerted on the actuating portion.

19. The medical device of claim 12, wherein the lumen is selectively removable and replaceable.

20. The medical device of claim 12, further comprising a source of a bone cement material that is fluidly coupled to the lumen for the bone cement material to pass through the lumen to exit at the distal end of the articulating portion.

* * * * *